US011382741B2

(12) United States Patent
Eidenschink et al.

(10) Patent No.: US 11,382,741 B2
(45) Date of Patent: Jul. 12, 2022

(54) DEVICES AND METHODS FOR SURGICAL VALVE EXPANSION

(71) Applicant: St. Jude Medical, Cardiology Division, Inc., St. Paul, MN (US)

(72) Inventors: Tracee Eidenschink, Wayzata, MN (US); Xiangyang Zhang, Maple Grove, MN (US); Nicholas V. Jepson, Buffalo, MN (US); Ryan J. Nesler, Mounds View, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 17/123,542

(22) Filed: Dec. 16, 2020

(65) Prior Publication Data

US 2021/0186689 A1    Jun. 24, 2021

Related U.S. Application Data

(60) Provisional application No. 62/949,550, filed on Dec. 18, 2019.

(51) Int. Cl.
*A61F 2/24*    (2006.01)

(52) U.S. Cl.
CPC .......... *A61F 2/2418* (2013.01); *A61F 2/2409* (2013.01); *A61F 2250/001* (2013.01); *A61F 2250/0071* (2013.01)

(58) Field of Classification Search
CPC ........ A61F 2/2418; A61F 2/2409; A61F 2/24; A61F 2/2445; A61F 2250/0004;
(Continued)

(56) References Cited

U.S. PATENT DOCUMENTS 3,755,823 A * 9/1973 Hancock ............... A61F 2/2418
623/2.18
4,626,255 A * 12/1986 Reichart ............... A61F 2/2418
623/2.15
(Continued)

FOREIGN PATENT DOCUMENTS

EP     1621162 A2    2/2006
WO  2012018779 A2   2/2012

OTHER PUBLICATIONS

Allen, K.B. et al., "Bioprosthetic Valve Fracture to Facilitate Transcatheter Valve-in-Valve Implantation", Ann Thorac Surg., Jun. 29, 2017, pp. 1501-1508.
(Continued)

*Primary Examiner* — Seema Mathew
(74) *Attorney, Agent, or Firm* — Wei & Sleman LLP

(57) ABSTRACT

A prosthetic heart valve includes a non-collapsible annular frame extending between an inflow edge and an outflow edge, the frame having a plurality of annularly spaced commissure posts adjacent the outflow edge. A valve assembly including a plurality of leaflets is connected to the frame. The frame includes a weakened portion such that the frame is expandable from an initial condition having a first diameter to an expanded condition having a second diameter larger than the first diameter when a radially outward force is applied to an inner surface of the frame. A stabilizing strut may be positioned adjacent the weakened portion to reinforce the frame. The prosthetic heart valve may include an expandable ring positioned around the expandable frame.

19 Claims, 15 Drawing Sheets

(58) Field of Classification Search
CPC .......... A61F 2250/0071; A61F 13/4963; A61F 2/2439; A61F 2/2442; A61F 2/06; A61F 2/2412; A61F 2/2475; A61F 2/86
See application file for complete search history.

(56) References Cited

U.S. PATENT DOCUMENTS

| | | | | |
|---|---|---|---|---|
| 5,037,434 | A * | 8/1991 | Lane | A61F 2/2418 623/2.18 |
| 5,549,665 | A * | 8/1996 | Vesely | A61F 2/2409 623/2.14 |
| 5,935,163 | A * | 8/1999 | Gabbay | A61F 2/2418 623/2.14 |
| 6,585,766 | B1 * | 7/2003 | Huynh | A61F 2/2412 623/2.38 |
| 7,585,321 | B2 | 9/2009 | Cribier | |
| 7,717,955 | B2 * | 5/2010 | Lane | A61F 2/2418 623/2.14 |
| 8,273,118 | B2 * | 9/2012 | Bergin | A61F 2/2427 623/2.11 |
| 8,613,765 | B2 | 12/2013 | Bonhoeffer et al. | |
| 9,414,913 | B2 * | 8/2016 | Beith | A61F 2/2409 |
| 9,504,556 | B2 | 11/2016 | Bebb et al. | |
| 9,510,944 | B2 | 12/2016 | Cai et al. | |
| 9,655,719 | B2 * | 5/2017 | Board | A61F 2/2418 |
| 10,080,653 | B2 | 9/2018 | Conklin et al. | |
| 10,130,469 | B2 | 11/2018 | Guttenberg et al. | |
| 10,543,085 | B2 * | 1/2020 | Chung | A61F 2/2409 |
| 11,071,626 | B2 * | 7/2021 | Colavito | A61F 2/2412 |
| 2006/0025855 | A1 * | 2/2006 | Lashinski | A61F 2/2409 623/2.1 |
| 2008/0147179 | A1 * | 6/2008 | Cai | A61L 27/3645 623/2.4 |
| 2012/0232646 | A1 * | 9/2012 | Agathos | A61F 2/2418 623/2.38 |
| 2013/0325116 | A1 * | 12/2013 | Sundler | A61F 2/2418 623/2.17 |
| 2014/0188221 | A1 * | 7/2014 | Chung | A61F 2/2409 623/2.18 |
| 2015/0366664 | A1 * | 12/2015 | Guttenberg | A61F 2/2412 623/2.17 |
| 2016/0030173 | A1 * | 2/2016 | Cai | A61L 27/3625 623/2.17 |
| 2016/0367365 | A1 * | 12/2016 | Conklin | A61F 2/2409 |
| 2017/0000604 | A1 * | 1/2017 | Conklin | A61F 2/2409 |
| 2017/0071732 | A1 * | 3/2017 | Conklin | A61F 2/2418 |
| 2017/0281342 | A1 | 10/2017 | Chung et al. | |
| 2018/0078366 | A1 | 3/2018 | Sievers et al. | |
| 2018/0289475 | A1 * | 10/2018 | Chung | A61F 2/2409 |
| 2019/0021854 | A1 | 1/2019 | Conklin et al. | |
| 2019/0083255 | A1 * | 3/2019 | Najm | A61F 2/2409 |
| 2019/0282360 | A1 | 9/2019 | Colavito et al. | |
| 2021/0346154 | A1 * | 11/2021 | Kaleta | A61F 2/2418 |

OTHER PUBLICATIONS

Extended European Search Report for Application No. 20215213.8, dated May 18, 2021, 10 pages.

* cited by examiner 1211  1207 1209  1216a
                1216b 1216c  1209  1208

DEVICES AND METHODS FOR SURGICAL VALVE EXPANSION

CROSS-REFERENCE TO RELATED APPLICATIONS

This application claims the benefit of the priority date of U.S. Provisional Patent Application No. 62/949,550, filed Dec. 18, 2019, the disclosure of which is hereby incorporated by reference herein.

BACKGROUND OF THE INVENTION

The present disclosure relates in general to a heart valve for heart valve replacement and, in particular, to bioprosthetic heart valves. More particularly, the present disclosure relates to surgical heart valves that facilitate the performance of subsequent valve-in-valve implantation procedures.

When a native heart valve in an individual is diseased or damaged, a bioprosthetic heart valve may be surgically implanted in that individual to replace the native heart valve. At some time after the bioprosthetic heart valve has been successfully implanted within the individual, the implanted heart valve may become damaged or worn out such that it ceases to function properly. If the implanted heart valve fails to function properly, a new replacement prosthetic heart valve may be surgically implanted to resume normal functions. However, at the point at which the original implanted heart valve needs replacement, patients are often too old and frail for another invasive surgical procedure. For these patients, a less traumatic valve-in-valve procedure (hereinafter referred to as "VIV procedure") may be performed. In a VIV procedure, a new prosthetic heart valve is implanted inside of the surgical heart valve using a minimally invasive transcatheter procedure.

One challenge that arises from VIV procedures is that the diameter of the surgical heart valve limits the size of the transcatheter heart valve that can be implanted inside of it. When the originally implanted surgical valve is small (e.g., 19 or 21 millimeters in diameter), the size of the implanted transcatheter heart valve may be too small to the meet the patient's blood flow requirements. This results in the phenomenon of patient-prosthesis mismatch (hereinafter referred to as "PPM"). PPM has shown to be associated with increased mortality after VIV procedures. Thus, there exists a need for a mechanism by which surgical heart valves can be expanded in vivo so that they can accept a sufficiently-sized transcatheter valve and minimize the potential for PPM.

BRIEF SUMMARY OF THE INVENTION

According to an embodiment of the present disclosure, a prosthetic heart valve includes a non-collapsible annular frame extending in a longitudinal direction between an inflow edge and an outflow edge. The frame has a plurality of annularly spaced commissure posts adjacent the outflow edge. A flow direction through the frame extends from the inflow edge toward the outflow edge. The frame has a deformable weakened portion such that the frame is expandable from an initial condition having a first diameter to an expanded condition having a second diameter larger than the first diameter when a radial outward force is applied to an inner surface of the frame. A valve assembly is connected to the frame and includes a plurality of leaflets.

In other embodiments, the frame may include a stabilizing strut positioned between the weakened portion and an associated commissure post. The stabilizing strut may have a substantially U-shape. The stabilizing strut may have a first height in the longitudinal direction in the initial condition of the frame and a second height in the longitudinal direction in the expanded condition of the frame, the first height being greater than the second height. The stabilizing strut may have a first width in a circumferential direction in the initial condition of the frame and a second width in the circumferential direction in the expanded condition of the frame, the first width being less than the second width. The stabilizing strut may have an apex positioned adjacent the weakened portion of the frame. The stabilizing strut may have an inverted substantially U-shape. The stabilizing strut may have a wave shape. The expanded condition, the stabilizing strut may be plastically deformed.

In yet other embodiments, the weakened portion may include a slit extending through a thickness of the frame. The slit may have a first width in a circumferential direction when the frame is in the initial condition and a second width in the circumferential direction when the frame is in the expanded condition, the second width being greater than the first width. The slit may be positioned between adjacent ones of the commissure posts in a circumferential direction of the frame. The slit may be positioned at a midpoint between the adjacent ones of the commissure posts. The slit may extend through the inflow edge and terminate at a position between the inflow edge and the outflow edge. The frame may include an inflow portion positioned below one of the commissure posts, the inflow portion extending from the inflow edge to a top edge, and the slit may extend through the inflow edge and terminate at a position between the inflow edge and the top edge. The slit may terminate at a rounded end having a perimeter enclosed within the inflow portion of the frame. The slit may extend through the inflow edge and the outflow edge of the frame. The frame may include an inflow portion positioned below one of the commissure posts, the inflow portion extending from the inflow edge to a top edge, and the entirety of the slit may be within the inflow portion of the frame such that the inflow edge and the top edge are uninterrupted by the slit. The slit may be spaced apart from the outflow edge and the inflow edge such that the inflow and outflow edges are uninterrupted by the slit.

In other embodiments, the weakened portion may include a plurality of perforations, each perforation extending through the thickness of the frame. The plurality of perforations may be spaced apart from each other in a linear array between the inflow edge and the outflow edge of the frame. Each of the plurality of perforations may have a diameter, and the diameters may increase sequentially in the longitudinal direction. Adjacent ones of the perforations may be spaced apart by a distance, and each of the distances may be less than 0.005 inches. The frame may include a pair of apertures extending through the frame, one of the apertures being positioned on one side of the weakened portion and another of the apertures being positioned on an opposite side of the weakened portion in a circumferential direction of the frame.

In still other embodiments, the prosthetic heart valve may further include an expandable ring positioned around an outer surface of the frame. The ring may include a weakened region that enables the ring to expand. The weakened region may include a slit extending through a thickness of the ring. The weakened region may include a through cut extending from a top edge of the ring to a bottom edge of the ring, and the ring may include at least one aperture on each side of the through cut. The prosthetic heart valve may further include a filament extending through the apertures of the ring and secured to the ring to maintain an annular shape of the ring.

DETAILED DESCRIPTION

As used herein in connection with a prosthetic heart valve, the term "inflow end" refers to the end of the heart valve through which blood enters when the valve is functioning as intended, and the term "outflow end" refers to the end of the heart valve through which blood exits when the valve is functioning as intended. As used herein, the terms "generally," "substantially," and "about" are intended to mean that slight deviations from absolute are included within the scope of the term so modified. Like numbers refer to similar or identical elements throughout. When used herein in the context of a prosthetic heart valve, or a component thereof, the circumferential direction refers to a direction extending along the circumference of the prosthetic heart valve.

Figure 1A:
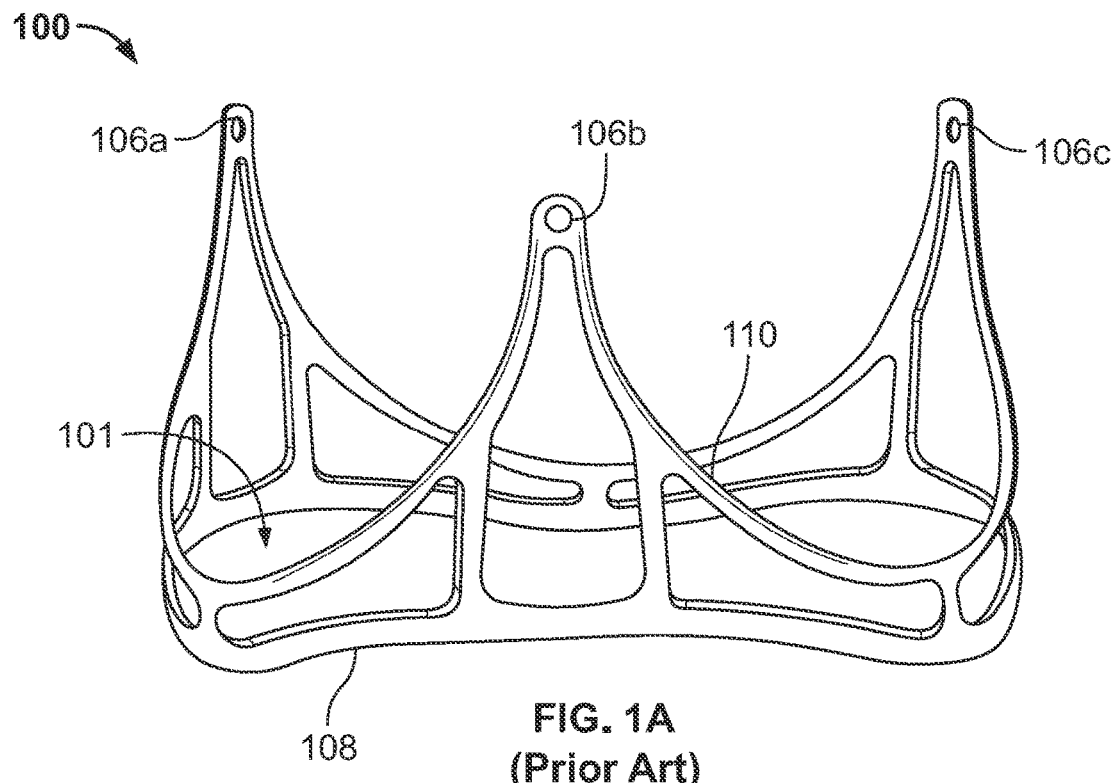
FIG. 1A is a perspective view of a frame of a surgical heart valve of the prior art.
Figure 1B:
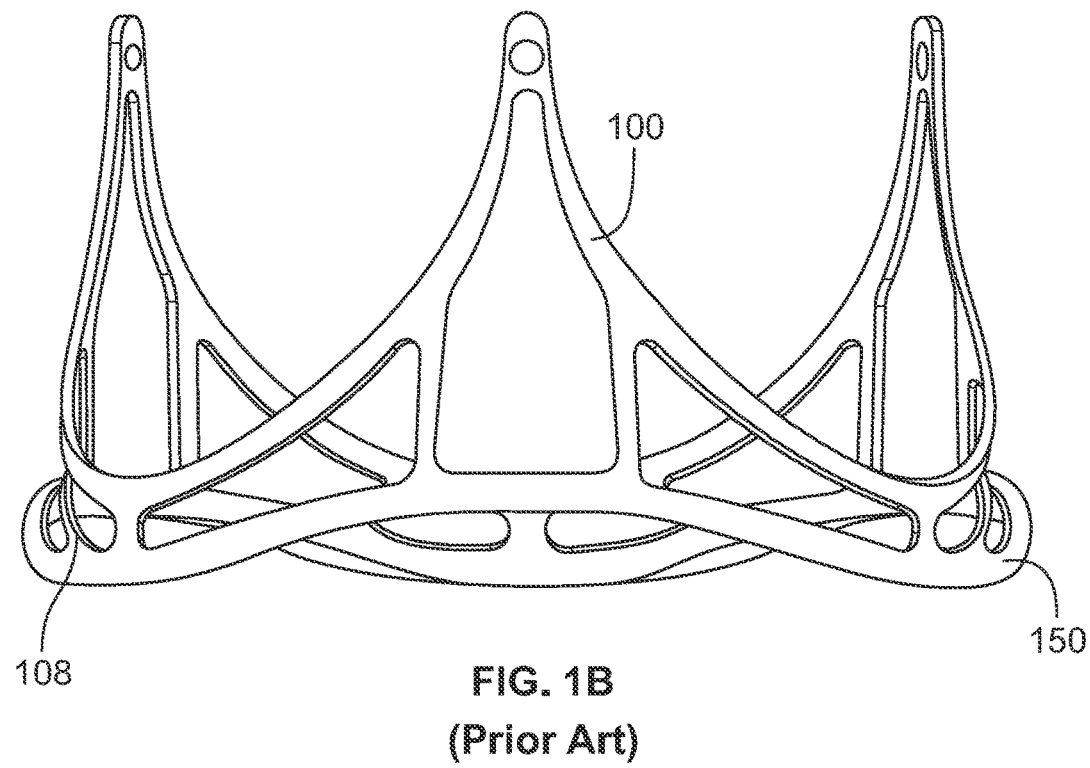
FIG. 1B is a perspective view of a frame having a support ring around the outer surface of the frame of the prior art.

FIG. 1A is a perspective view of a frame 100 for a prosthetic heart valve according to the prior art. Frame 100 is a component of a surgical heart valve, i.e., a prosthetic heart valve that is implanted in a patient through open chest, open heart surgery. Generally, certain embodiments of the present disclosure include frames similar to frame 100, although each embodiment includes a different feature that enables the frame to expand after implantation, in vivo, as will be described in further detail below. Expansion of the frame enables a sufficiently large transcatheter valve to be implanted within the surgical heart valve during a VIV procedure.

Referring to FIG. 1A, frame 100 is a hollow, non-collapsible annular stent-like structure. Frame 100 is referred to as "hollow" because the interior region 101 that is bounded by its annular structure is open. Frame 100 is typically made of a biologically compatible metal, such as titanium (e.g., Ti 6Al-4V ELI Grade 23) or Elgiloy MP35N. A typical technique for making frame 100 is to cut it from a tube using a laser. Frame 100 is then typically electro-polished. Alternatively, frame 100 may be made from other biologically compatible materials, such as polymers, including polyetheretherketone or acetal, or a combination of metal and polymer.

Because the prosthetic heart valve being discussed is a tricuspid valve (e.g., for use in replacing a patient's aortic valve), frame 100 has three commissure posts 106a, 106b, and 106c that may be equally spaced from one another around the circumference of the frame. Each commissure post stands up from the annularly continuous base portion of the frame. The base portion includes a lower-most, blood-inflow portion 108. As used throughout the present description, the terms lower, below, upper, above, bottom and top refer to a frame oriented as shown in FIG. 1A. Inflow portion 108 may be scalloped as one proceeds around the frame to approximately match the natural scallop of the native valve annulus. In particular, the scallop of inflow portion 108 may rise in the vicinity of each commissure post 106, and may fall between each annularly adjacent pair of commissure posts.

Frame 100 also includes an annularly continuous blood-outflow portion 110 (which merges with and becomes part of each commissure post 106). Outflow portion 110 may be much more deeply scalloped than inflow portion 108. In particular, outflow portion 110 rises adjacent each commissure post 106 (actually merging into each commissure post), and falls between each annularly adjacent pair of commissure posts.

Inflow portion 108, outflow portion 110, and the flexibility of frame 100 are designed to help ensure proper opening and coaptation of the finished valve in use. (Coaptation is the coming together of the outflow portions of the valve leaflets when the valve is closed.) Frame 100 is further designed to decrease maximum stresses in the frame in use, which gives the finished valve an increased safety factor.

Figure 2:
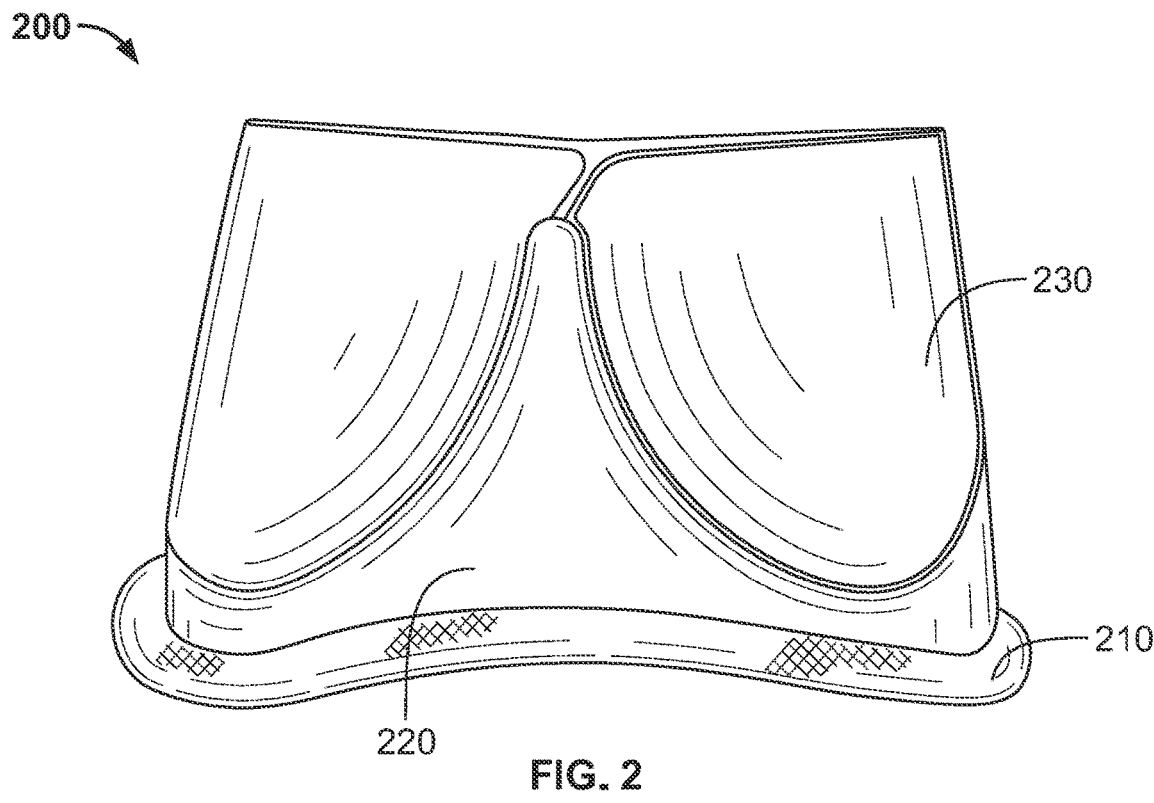
FIG. 2 is a perspective view of an embodiment of a surgical heart valve of the prior art.

FIG. 2 illustrates a prior art prosthetic heart valve 200 formed from frame 100. Prosthetic heart valve 200 may include a sewing cuff 210 and one or more layers of fabric and/or biological tissue covering the sewing cuff and frame 100. For example, a ring (not shown) formed of silicone or another appropriate material may be positioned around the outside of inflow portion 108 and may follow the scalloping of the inflow portion. A layer of fabric (not shown) may then be applied tightly over the inside surface of frame 100, over the outside surface of the frame, and around the exposed surfaces of the ring so that the fabric layer conforms to the outflow portion 110 of the frame. Sutures may be used to hold the fabric layer to the underlying structures.

Optionally, a fabric sleeve (not shown) may be sutured or otherwise attached to cover the top of each commissure post 106 prior to the application of the fabric layer. These fabric sleeves may help reduce the possibility that the tips of the commissure posts will poke through the fabric layer or any subsequently applied layers.

A layer of biological tissue 220 may then be applied over the fabric layer both inside and outside of frame 100 and may attach to the fabric-covered ring. The biological tissue may be mammalian pericardial tissue, such as bovine, porcine or equine pericardium, or other appropriate types of tissue. The tissue layer may be secured to the underlying structure by sutures. Additional tissue, preferably of the same type, may be cut to shape and assembled to the interior of the covered frame to form leaflets 230. The lower edges of the leaflets may follow the scalloped shape of inflow portion 108. All three leaflets shown in FIG. 2 may be formed from a single integral sheet of tissue. Rather than biological tissue, leaflets 230 and the outer covering of prosthetic heart valve 200 may be formed from a biocompatible polymer, or from a tissue/polymer combination. The various layers that may be applied to frame 100 to form surgical heart valve 200 are more fully described in U.S. Pat. No. 9,510,944, the disclosure of which is hereby incorporated by reference herein.

Figure 3:
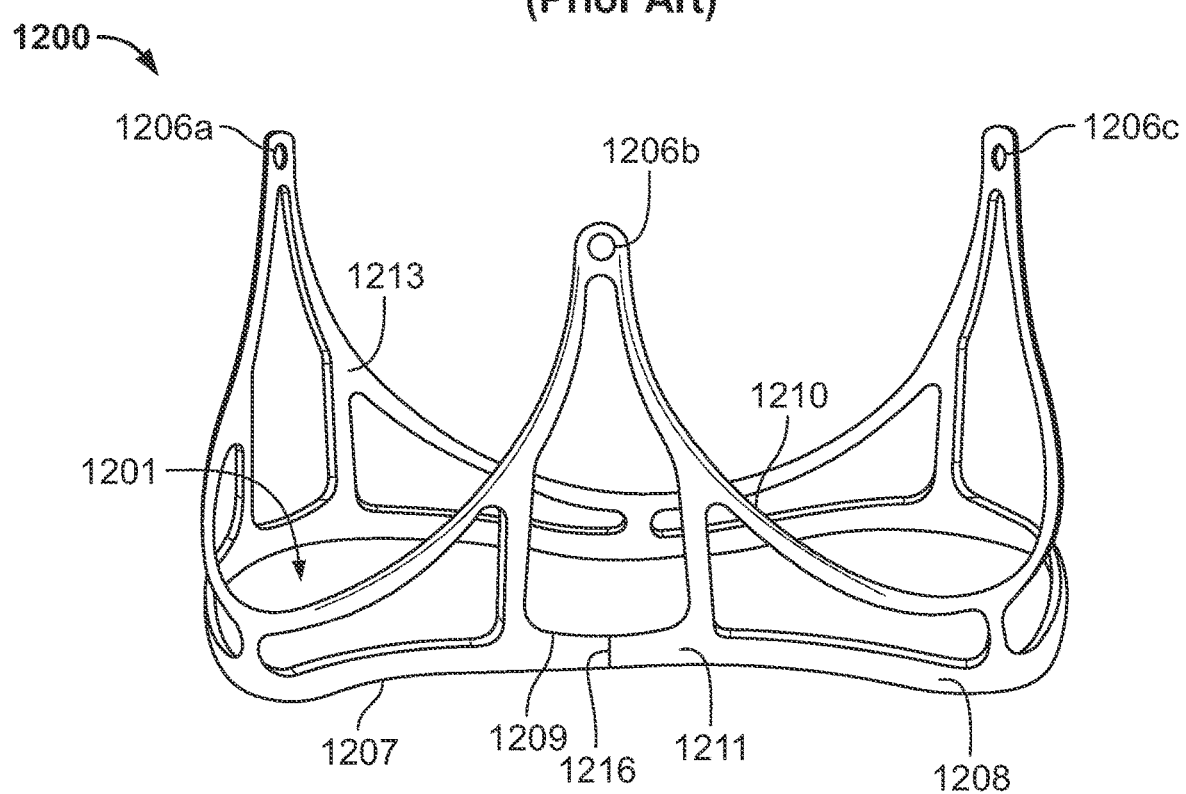
FIG. 3 is a perspective view of a frame of a prosthetic heart valve according to an embodiment of the present disclosure.

The prosthetic heart valves in accordance with the present disclosure may be similar to heart valve 200 described above, and may include the same fabric, tissue and/or polymer leaflets and covering layers, but may be modified to include features that allow the frame of the valve to expand after implantation, during a VIV procedure. Referring to FIG. 3, a frame 1200 that may be part of a surgical heart valve is similar in structure to frame 100, although frame 1200 includes expansion features that allow the frame to expand after implantation. One form of expansion feature may be the inclusion of at least one weakened portion in frame 1200. In the illustrated embodiment, the weakened portion is a groove or slit 1216 scored or otherwise cut into the frame at a position below a commissure post 1206, although the slit can be positioned at other locations on the frame. FIG. 3 shows one such slit 1216 formed in frame 1200, although a greater number of slits may be employed. Slit 1216 may be incorporated in frame 1200 at the time of manufacture (for example, by laser cutting the slits into the metal tube) or by adding the slits to a previously fabricated frame (for example, by laser cutting, mechanically cutting, grinding or otherwise processing the tube to form the grooves therein).

Slit 1216 extends along the height of the inflow portion 1208 of frame 1200 from an inflow or bottom edge 1207 to a top edge 1209, but in other embodiments may only extend along a portion of the height of the inflow portion. Slit 1216 may extend entirely through the thickness of frame 1200 and allow the frame to separate at that location to enable the frame to expand. Alternatively, the slit may be in the form of a score that does not extend through the entire thickness of the frame, which would allow preferential breaking of the frame at that position. Slits 1216 may have any height (measured between inflow edge 1207 and top edge 1209), depth (measured between the outer surface 1211 and inner surface 1213 of frame 1200), and width (measured along the circumference of the frame) that allows the frame to break in a desired manner. In a preferred embodiment, slit 1216 has a width of about 0.001 inches in the circumferential direction of frame 1200.

Figure 4:
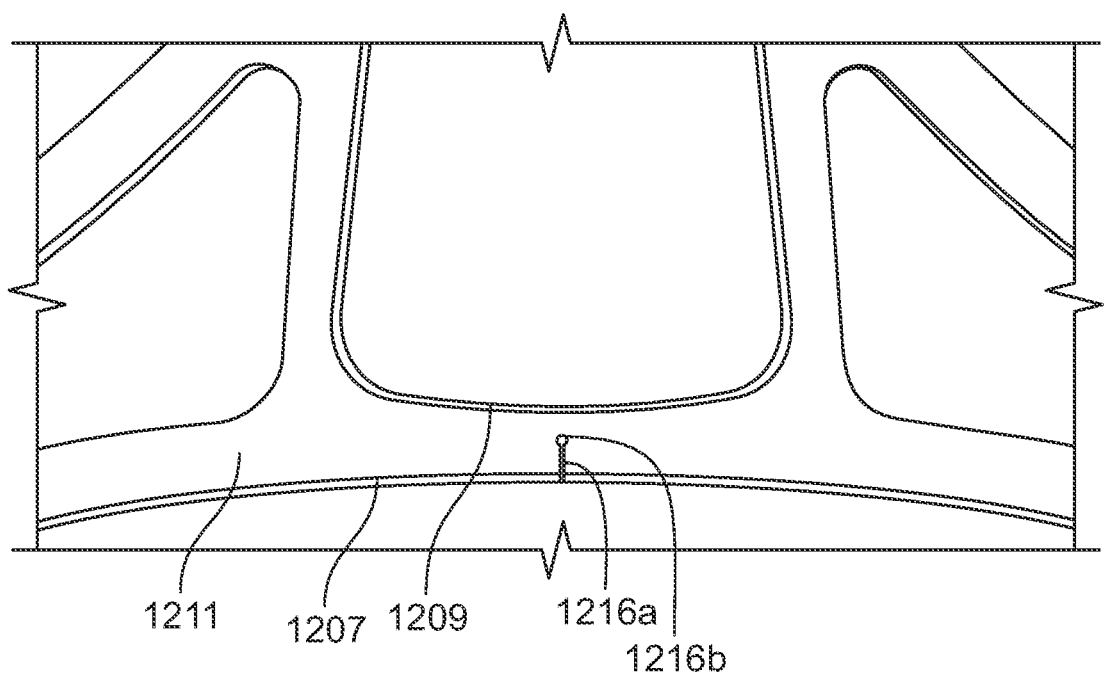
FIG. 4 is an enlarged view of a weakened portion of a frame according to another embodiment of the present disclosure.

As shown in FIG. 4, an alternative embodiment of frame 1200 includes a slit 1216 having a straight portion 1216a which has a first end extending through inflow edge 1207 and a second or closed end spaced from both the inflow edge and top edge 1209. The second end of slit 1216 connects to a rounded portion 1216b having a diameter larger than the width of straight portion 1216a. Rounded portion 1216b is designed to alleviate the high stresses at the second or closed end of slit 1216.

Figure 5:
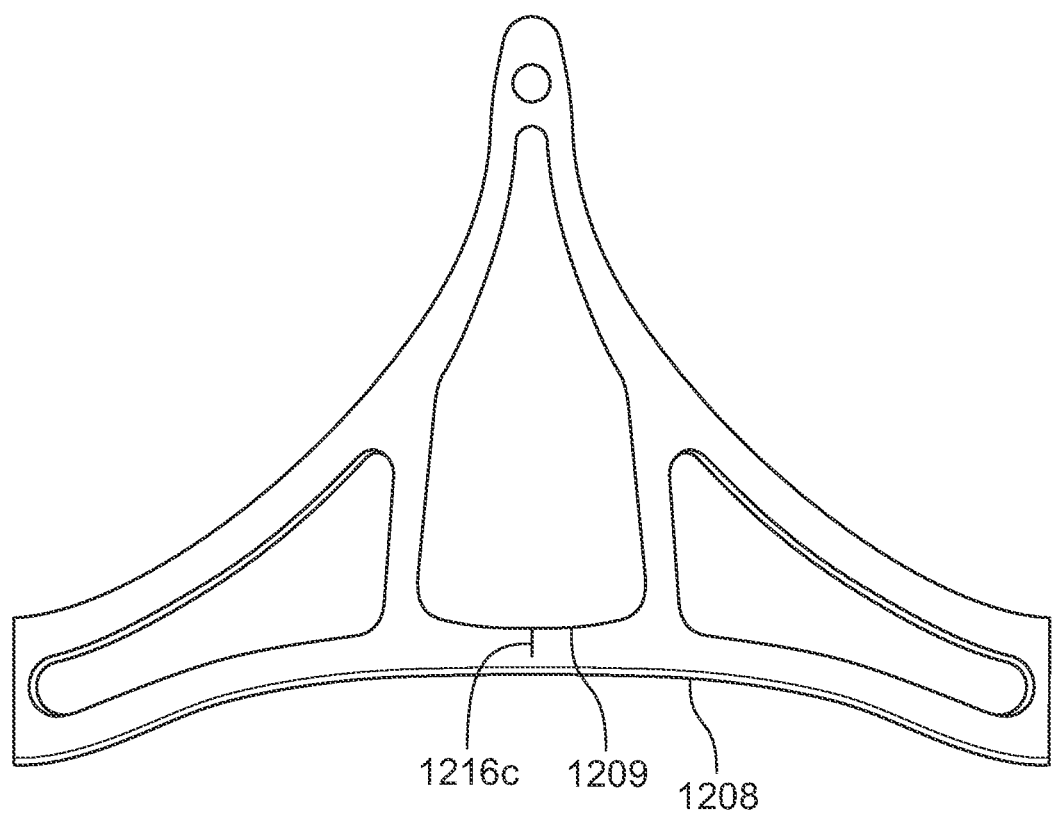
FIG. 5 is a partial side view of a frame having a weakened portion according to a further embodiment of the present disclosure.
Figure 6:
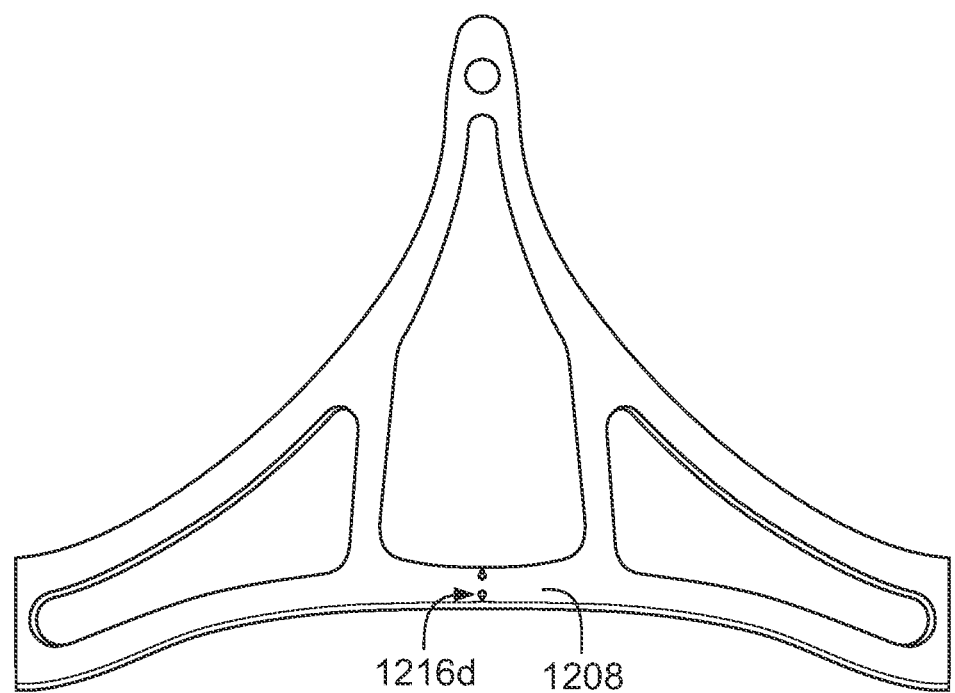
FIGS. 6 and 7 are partial side views of frames having weakened portions according to additional embodiments of the present disclosure.
Figure 7:
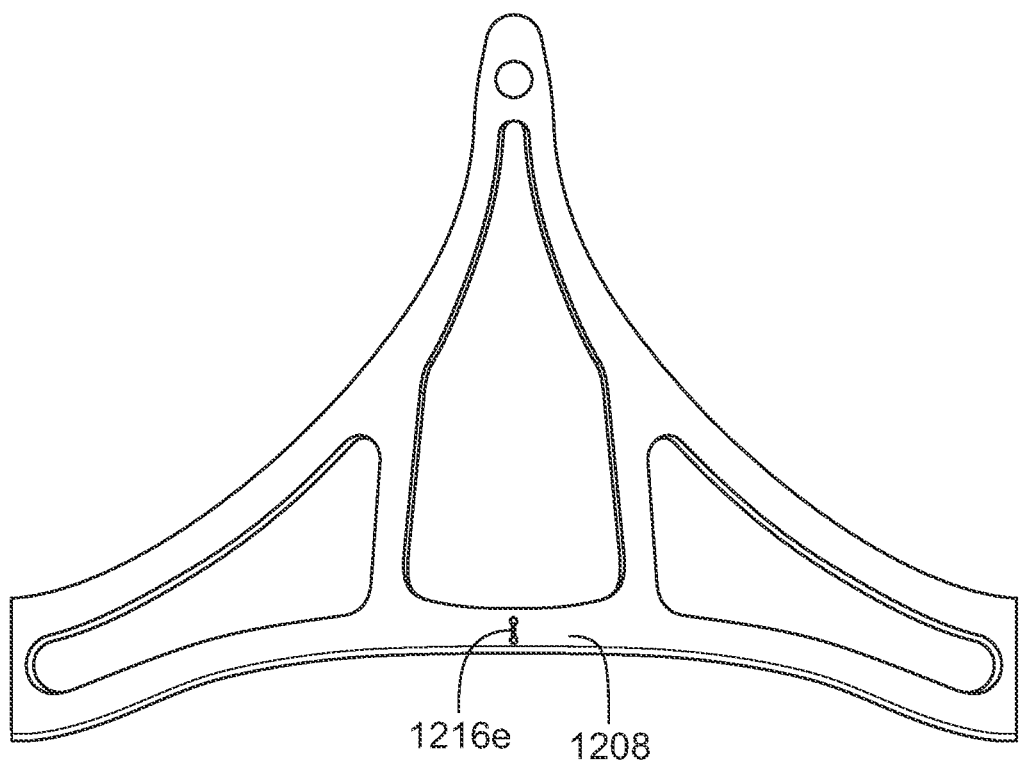

Although shown in FIG. 4 as extending only through the inflow edge 1207 of frame 1200, a slit 1216c may alternatively extend only through top edge 1209, as shown in FIG. 5, or may extend through both the inflow edge and the top edge, as shown in FIG. 6. Referring to FIG. 6, slit 1216d may have a first section that extends through inflow edge 1207 and a second section that extends through top edge 1209, but the first and second sections may not meet one another such that frame 1200 remains connected in a region between the first and second sections of the slit. In the illustrated embodiment, each of the sections of slit 1216d includes a rounded portion at its closed end spaced from the edge of inflow portion 1208. Referring to FIG. 7, slit 1216e is formed of a straight portion which terminates at both ends in a rounded portion. Thus, neither end of slit 1216e extends through an edge of inflow portion 1208.

Figure 8:
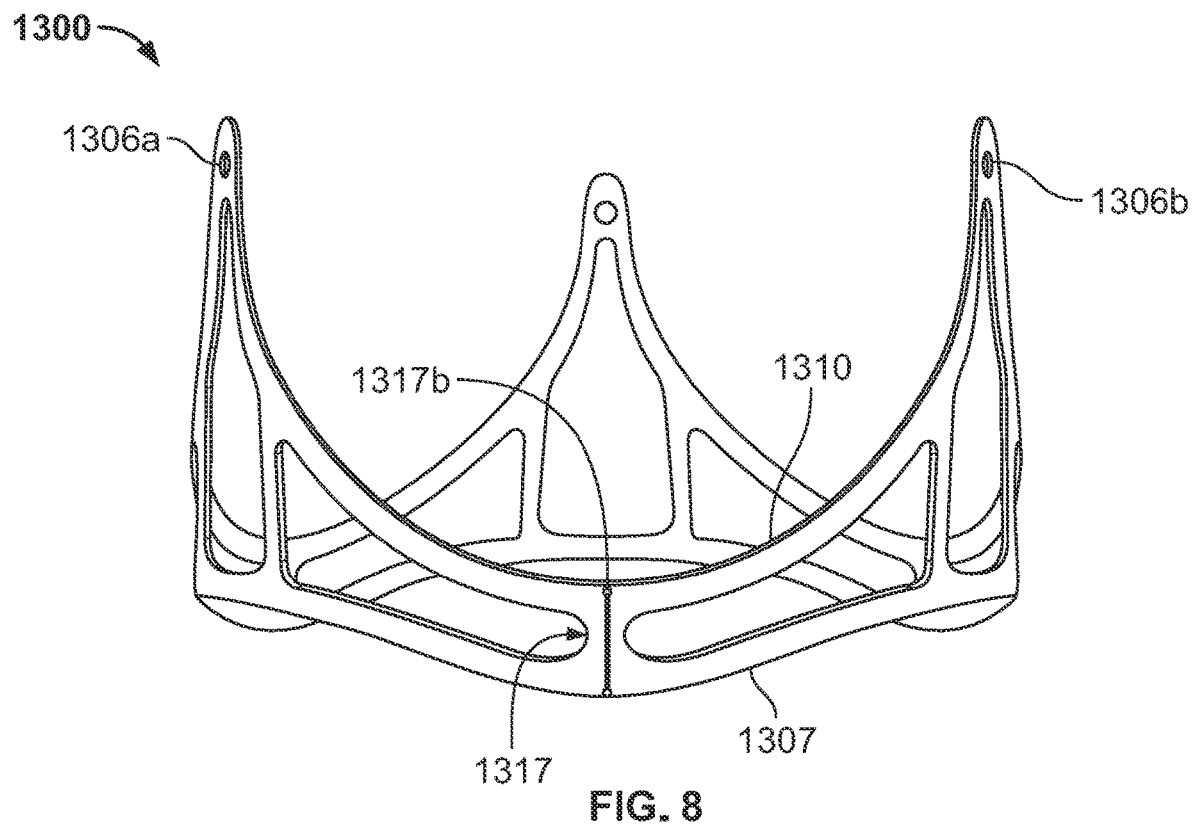
FIGS. 8-14 are side views of frames having weakened portions according to additional embodiments of the present disclosure.
Figure 9:
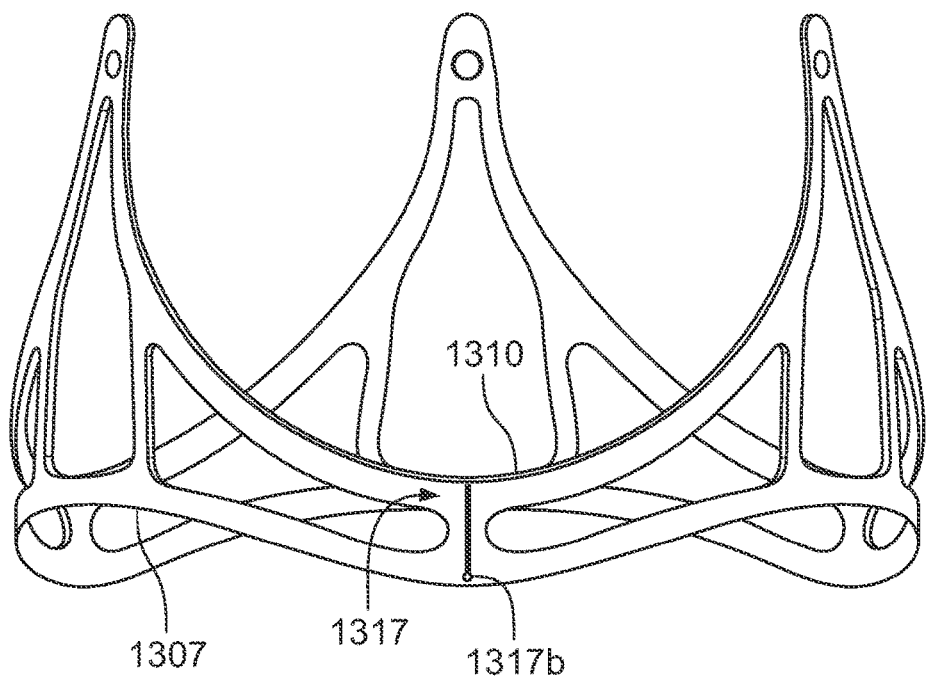
Figure 10:
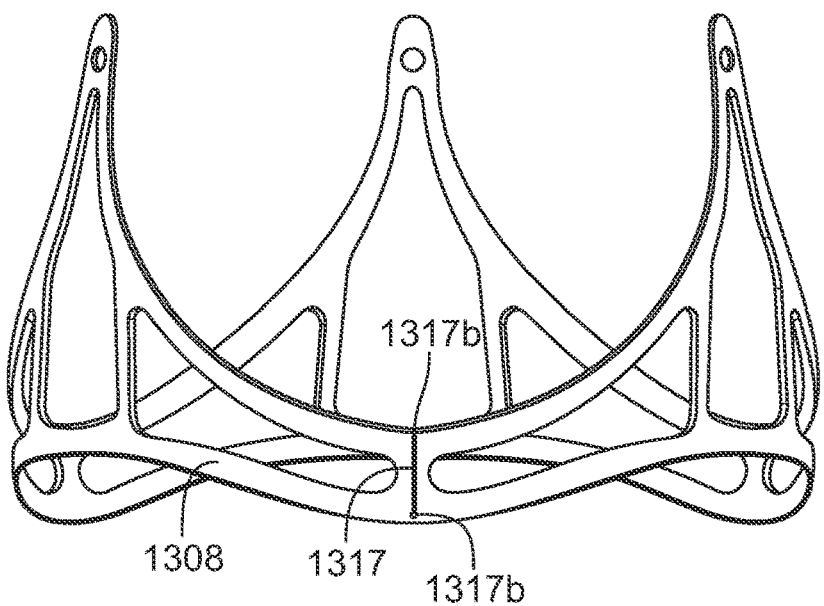

FIGS. 8-15 show alternative embodiments of a frame 1300 substantially similar to frame 1200, with a weakened portion enabling expansion of the frame. However, the weakened portions are positioned on frame 1300 in a region circumferentially between two commissure posts 1306a and 1306b and extend between and/or through inflow edge 1307 and outflow edge 1310. Frame 1300 has one or more slits 1317 that function in substantially the same manner as slits 1216 described above. In FIG. 8, slit 1317 is positioned at about the midpoint between commissure posts 1306a and 1306b. Although only a single slit 1317 is shown in FIGS. 8-10, frame 1300 may have multiple such slits, such as at the midpoint between each pair of commissure posts 1306. Further, although slit 1317 is shown as extending through both inflow edge 1307 and outflow edge 1310, slit 1317 can have any of the configurations described above for slit 1216.

FIG. 8 shows slit 1317 extending through inflow edge 1307 and terminating at rounded portion 1317b spaced from both the inflow edge and outflow edge 1310 such that outflow edge 1310 remains connected. FIG. 9 shows slit 1317 extending through outflow edge 1310 and terminating at rounded portion 1317b spaced apart from inflow edge 1307 and outflow edge 1310 such that inflow edge 1307 remains connected. FIG. 10 shows slit 1317 terminating within inflow portion 1308 without extending through an inflow or outflow edge of the inflow portion.

Figure 11:
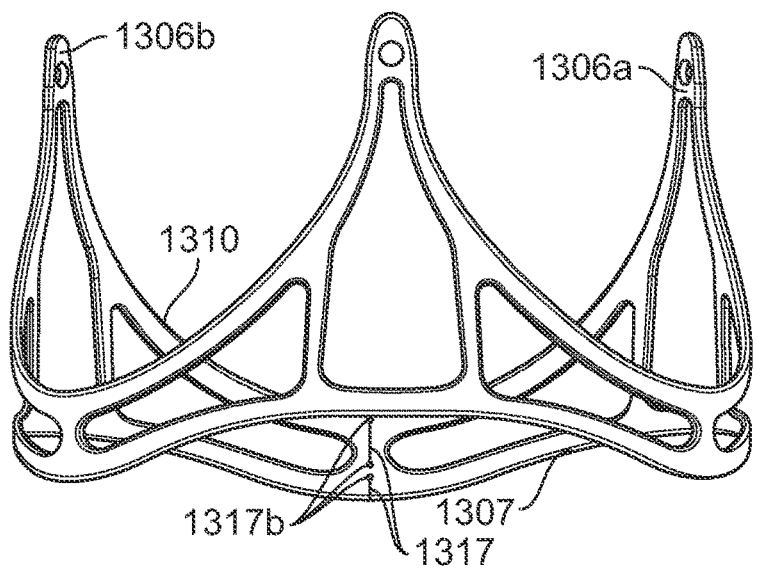
Figure 12:
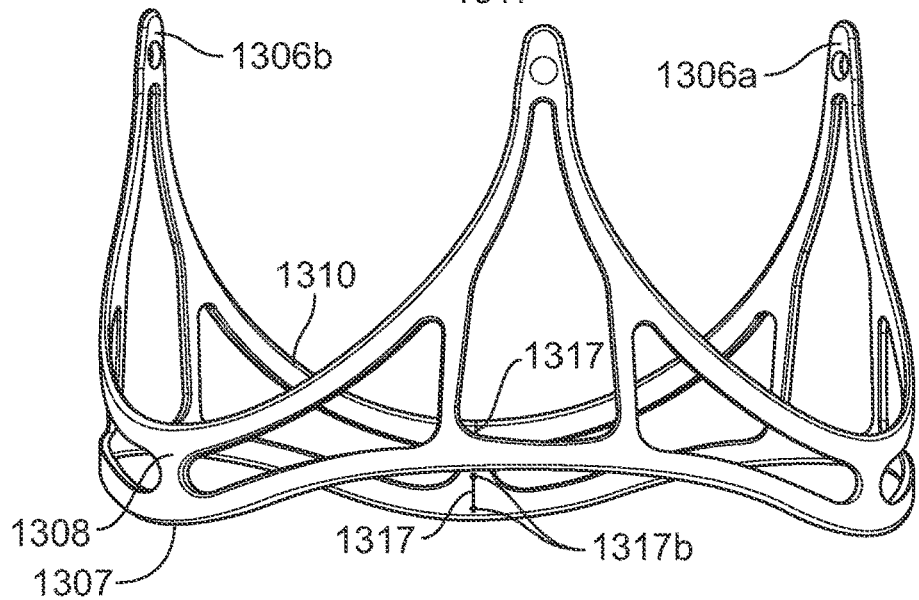

FIGS. 11 and 12 show a variant of frame 1300 having multiple longitudinally aligned slit sections 1317 positioned between commissure posts 1306a and 1306b. FIG. 11 shows a first slit section 1317 extending through inflow edge 1307 and a second slit section 1317 positioned between the first slit section and outflow edge 1310, although the second slit section 1317 does not extend through outflow edge 1310. FIG. 12 shows a first slit section 1317 extending through outflow edge 1310 and a second slit section 1317 positioned between the first slit section and inflow edge 1307, although the second slit section 1317 does not extend through inflow edge 1307.

Figure 13:
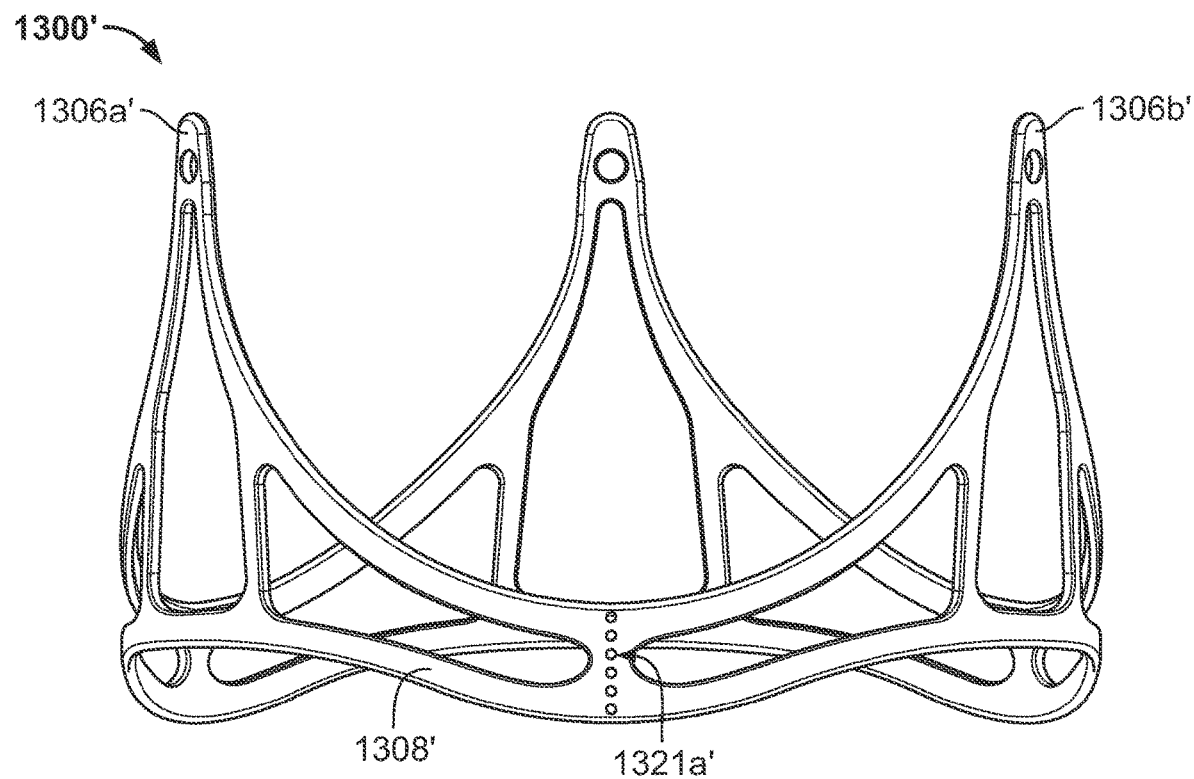
Figure 14:
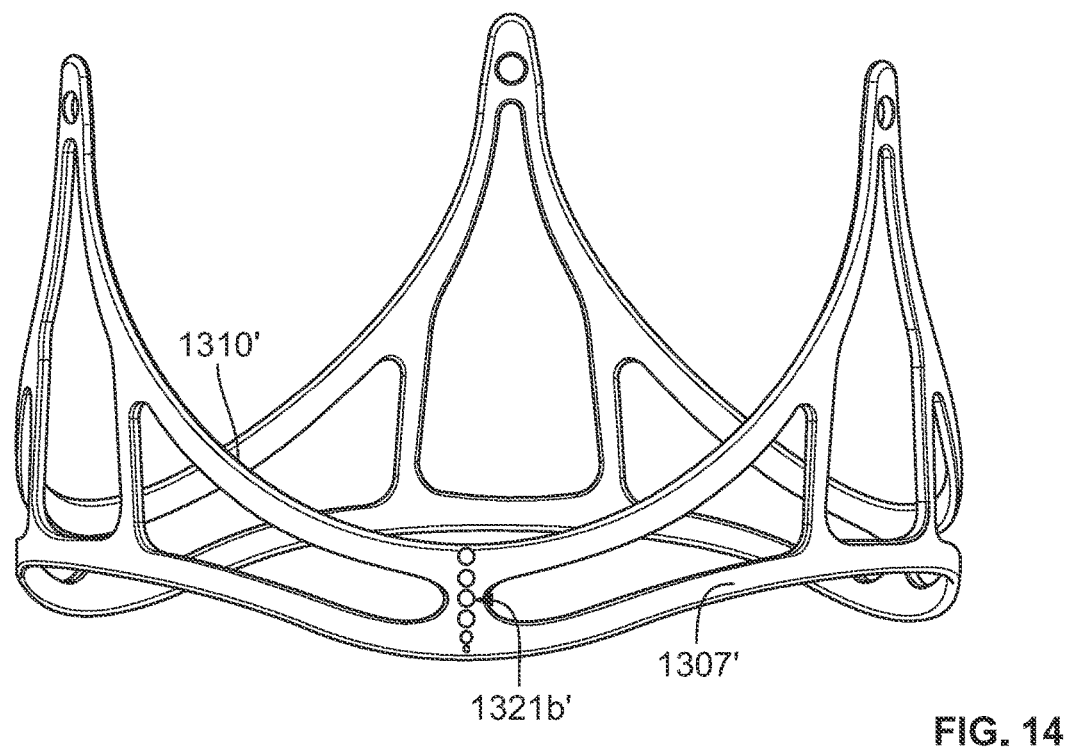
Figure 15:
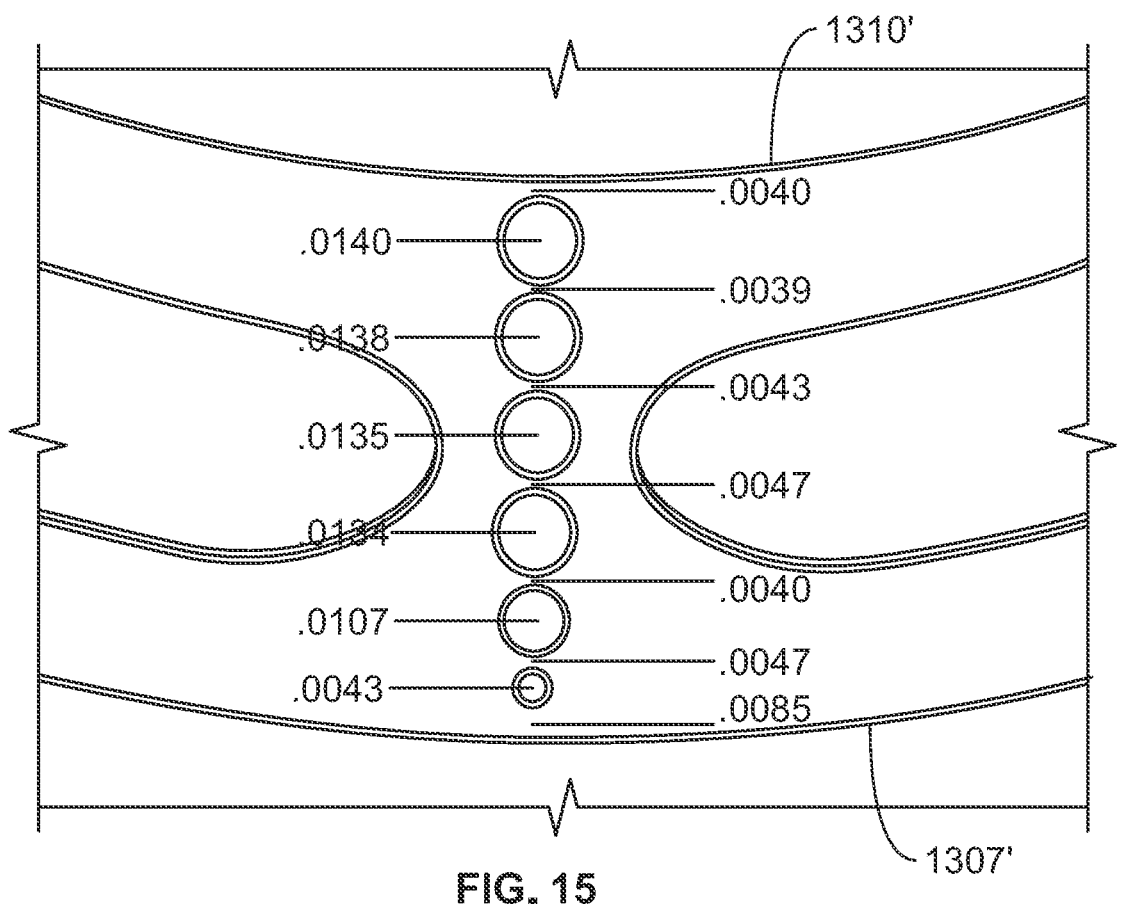
FIG. 15 is an enlarged view of the weakened portion of the frame of FIG. 14.

FIGS. 13-15 show a frame 1300' having at least one weakened portion in the form of spaced apart perforations 1321a' extending in a generally straight line along the height of the frame at a midpoint between commissure posts 1306a' and 1306b'. In one embodiment, perforations 1321a' may each be round, equally sized and equally spaced apart from one another along the height of the frame, as shown in FIG. 13. In other embodiments, shown in FIGS. 14 and 15, frame 1300' may have a weakened portion in the form of spaced apart perforations 1321b' having sequentially increasing diameters, with the smallest diameter perforation closest to the inflow edge 1307' of frame 1300' and the largest diameter perforation closest to outflow edge 1310'. The diameters of perforations 1321b' may range from about 0.0043 inches to about 0.0140 inches. Further, in this embodiment, perforations 1321b' may not be equally spaced apart from one another, as shown in FIG. 15. Although FIGS. 13-15 show perforations 1321a' and 1321b' aligned with one another in a linear array, that need not be the case. Perforations 1321a' and 1321b' may be offset from one another as long as the distance between adjacent ones of the perforations is appropriate to not negatively impact the ability of frame 1300' to break and expand in a controlled manner.

Figure 16:
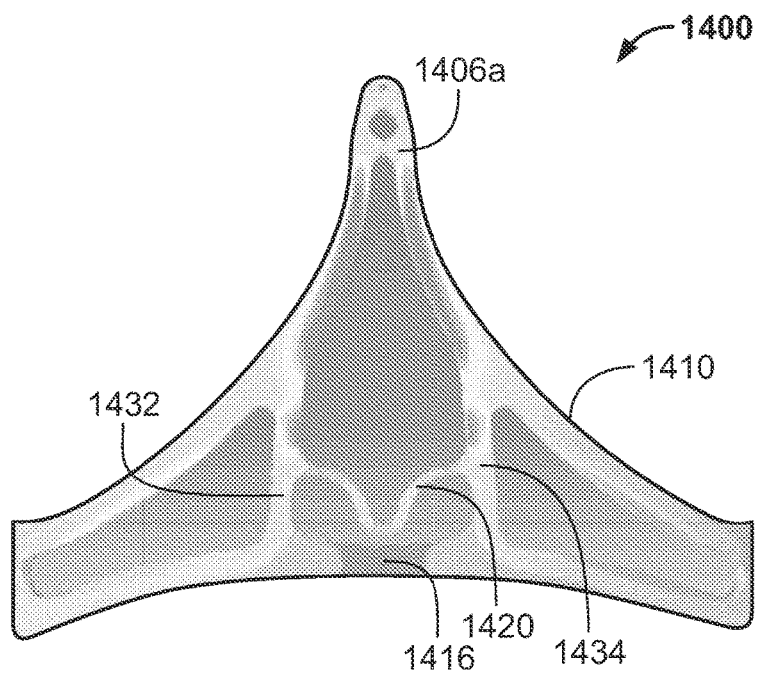
FIG. 16 is a partial side view of a prosthetic heart valve frame having stabilizing struts according to an embodiment of the present disclosure.
Figure 17:
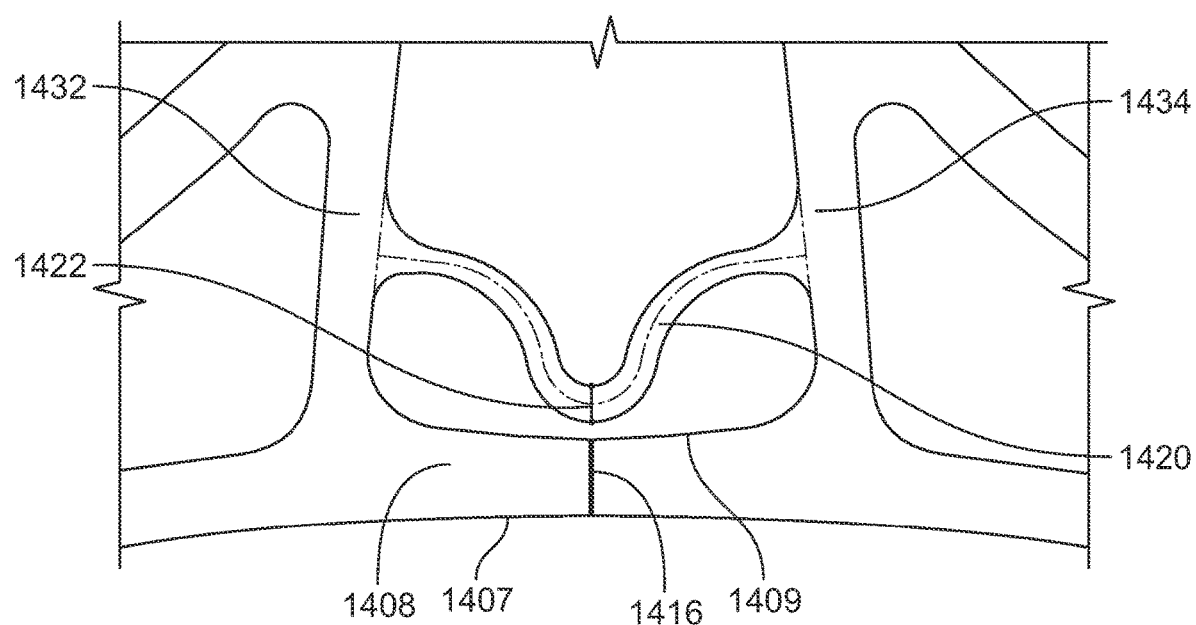
FIG. 17 is an enlarged view of a portion of the frame of FIG. 16.
Figure 18:
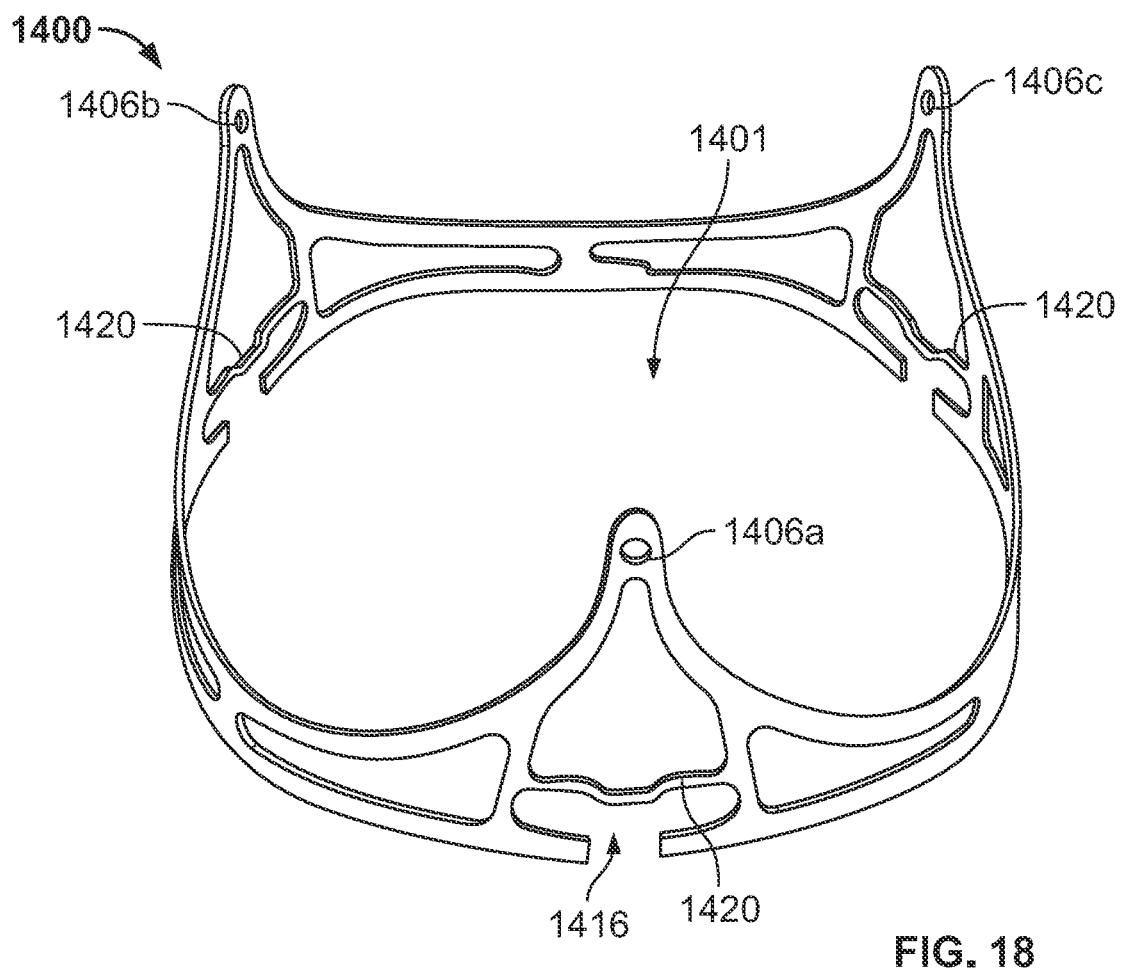
FIG. 18 is a top perspective view of the frame of FIG. 16 in an expanded condition.

FIGS. 16-18 show a frame 1400 which includes a slit 1416 extending through inflow portion 1408 from inflow edge 1407 to top edge 1409 in a position below commissure post 1406a. Slit 1416 extends fully through the thickness of frame 1400 and allows for expansion of the frame when an outward pressure is exerted from interior region 1401. Frame 1400 includes struts 1432 and 1434 that connect commissure post 1406a to the inflow portion 1408 of the frame at top edge 1409. Struts 1432 and 1434 extend substantially in a direction defined from the inflow edge 1407 to the outflow edge 1410 of frame 1400. Slit 1416 is positioned at approximately the midpoint between struts 1432 and 1434. Frame 1400 also includes a stabilizing strut 1420 that extends between and connects struts 1432 and 1434. FIG. 17 shows an enlarged view of stabilizing strut 1420 which is generally wave-shaped or U-shaped and includes an apex 1422 that extends toward inflow portion 1408. Stabilizing strut 1420 is positioned between slit 1416 and commissure post 1406a such that apex 1422 is directly above slit 1416. The material forming stabilizing strut 1420 may have a width of between about 0.005 inches and about 0.020 inches, preferably between about 0.010 inches and about 0.015 inches. While stabilizing strut 1420 generally has a wave shape, the curved shape of the strut may vary, as may its height and/or width. Stabilizing strut 1420 reinforces frame 1400, enhances its radial stiffness, and reduces the stresses on the frame during expansion. While a single slit 1416 and a single stabilizing strut 1420 have been described in association with commissure post 1406a, frame 1400 may have additional slits and stabilizing struts spaced around is circumference. For example, frame 1400 may have three slits 1416 and three stabilizing struts 1420, one associated with each commissure post 1406, as shown in FIG. 18. Also, while frame 1400 has been described as including a slit 1416 that extends through inflow portion 1408 from inflow edge 1407 to top edge 1409, any of the slits or weakened portions described above may be used in combination with stabilizing struts 1420. FIG. 18 shows frame 1400 in an expanded state. In the illustrated embodiment, frame 1400 includes three slits 1416 paired respectively with three stabilizing struts 1420, with one pair under each commissure post 1406a, 1406b, and 1406c. The apex 1422 of each stabilizing strut 1420 is positioned directly above a respective slit 1416. As discussed above, frame 1400 is expandable by, for example, a balloon while implanted within a patient. In this embodiment, frame 1400 begins expanding at about 2 atmospheres of pressure and is fully expanded by about 8 atmospheres. In an expanded condition, slits 1416 may widen to a width in the circumferential direction of about 0.079 inches. As the widths of slits 1416 increase, the sides of U-shaped stabilizing struts 1420 move away from one another, flattening the shape of the stabilizing struts while reinforcing frame 1400. The maximum stress withstood by frame 1400 may be between about 300 Mpa and about 520 MPa, and generally between about 330 MPa and about 385 MPa.

Figure 19:
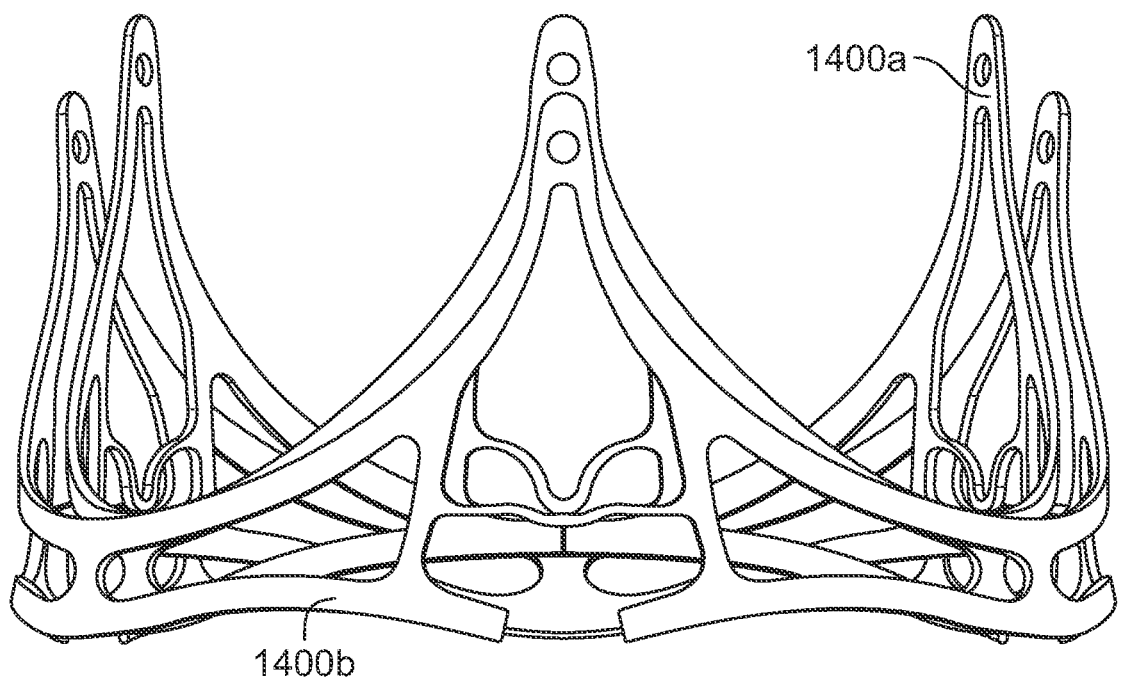
FIG. 19 illustrates overlapping side views of the frame of FIG. 16 in the initial and expanded conditions.

FIG. 19 shows a comparison of frame 1400 in an initial, unexpanded condition 1400a and a final, expanded condition 1400b. As shown, frame 1400 reduces in height as slits 1416 widen to increase the diameter of the frame. It can also be seen that stabilizing struts 1420 also widen and reduce in height as frame 1400 is expanded to help maintain the frame in the expanded condition. With stabilizing struts 1420, frame 1400 remains highly durable and maintains about 80% of its radial force.

Figure 20:
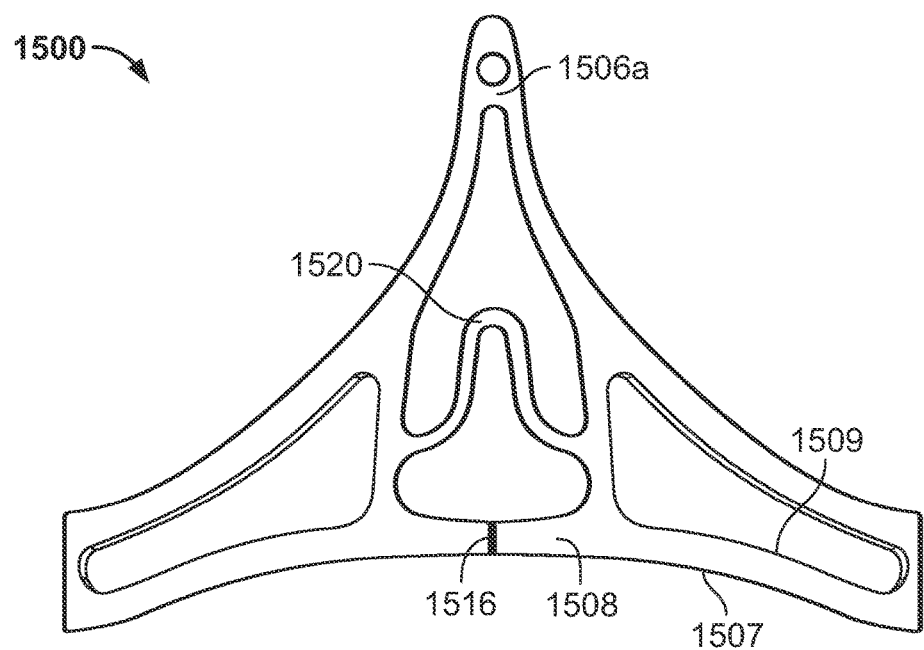
FIG. 20 is a partial side view of a prosthetic heart valve frame having stabilizing struts according to another embodiment of the present disclosure.

FIG. 20 shows a frame 1500 having an alternative embodiment of a stabilizing strut 1520. Strut 1520 has an inverted U-shape which generally mimics the rise and fall of commissure post 1506a. Frame 1500 includes a slit 1516 that extends through inflow portion 1508 from inflow edge 1507 to top edge 1509 and that is positioned below commissure post 1506a. However, any of the slits or other weakened portions described above may be utilized in place of the illustrated slit 1516. Stabilizing strut 1520 generally has a wave shape, although the curved shape of the strut may vary, as may its height and/or width.

Figure 21:
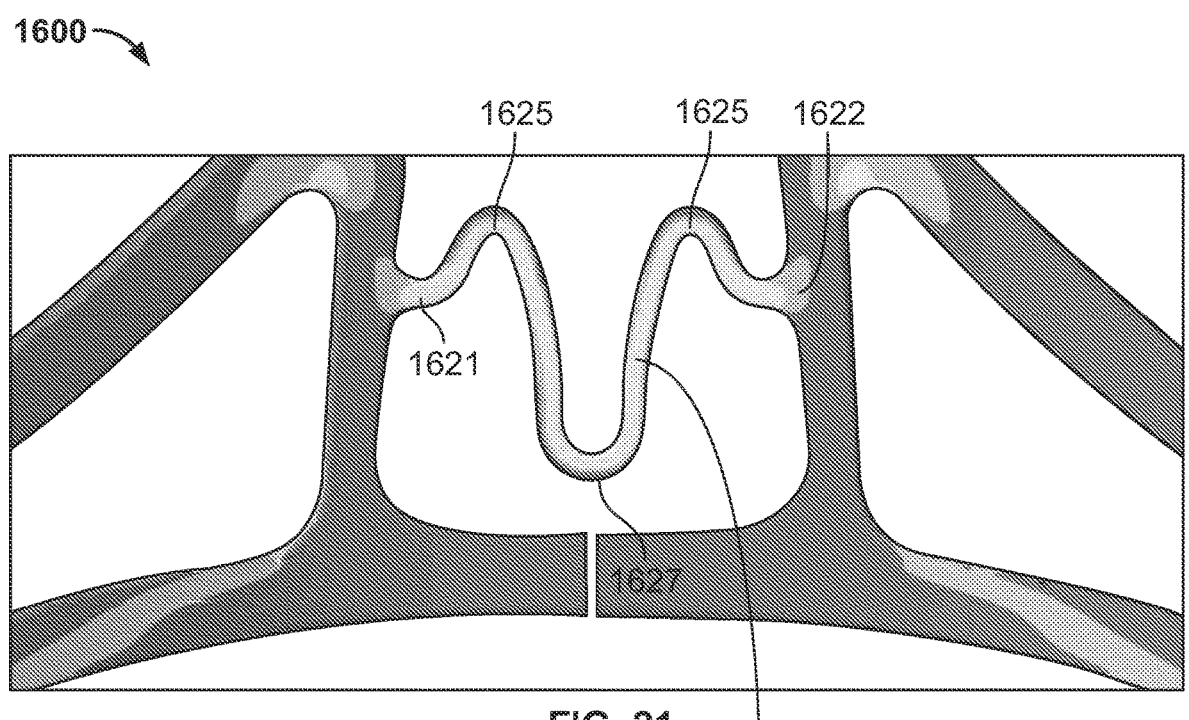
FIGS. 21 and 22 are enlarged partial views of prosthetic heart valve frames having stabilizing struts in accordance with alternative embodiments of the present disclosure.

FIG. 21 illustrates an alternative embodiment of a frame 1600 with one or more stabilizing struts 1620. In this embodiment, each stabilizing strut 1620 has a generally wave shape. Stabilizing strut 1620 extends between first end 1621 and second end 1622, each end being connected to the frame. First and second ends 1621, 1622 each extend into a peak 1625 such that stabilizing strut 1620 includes two peaks 1625 and a trough 1627 positioned between the peaks. In the illustrated embodiment, peaks 1625 are substantially identical to each other, such that the peaks have the same height and substantially the same width, measured in the circumferential direction of the frame. Trough 1627 connects the adjacent peaks 1625 and spans a greater distance in the height direction than do peaks 1625. As a result of its configuration, stabilizing strut 1620 has a greater length between first end 1621 and second end 1622. Such an embodiment allows for greater deformation of frame 1600 without the breaking of stabilizing strut 1620.

Figure 22:
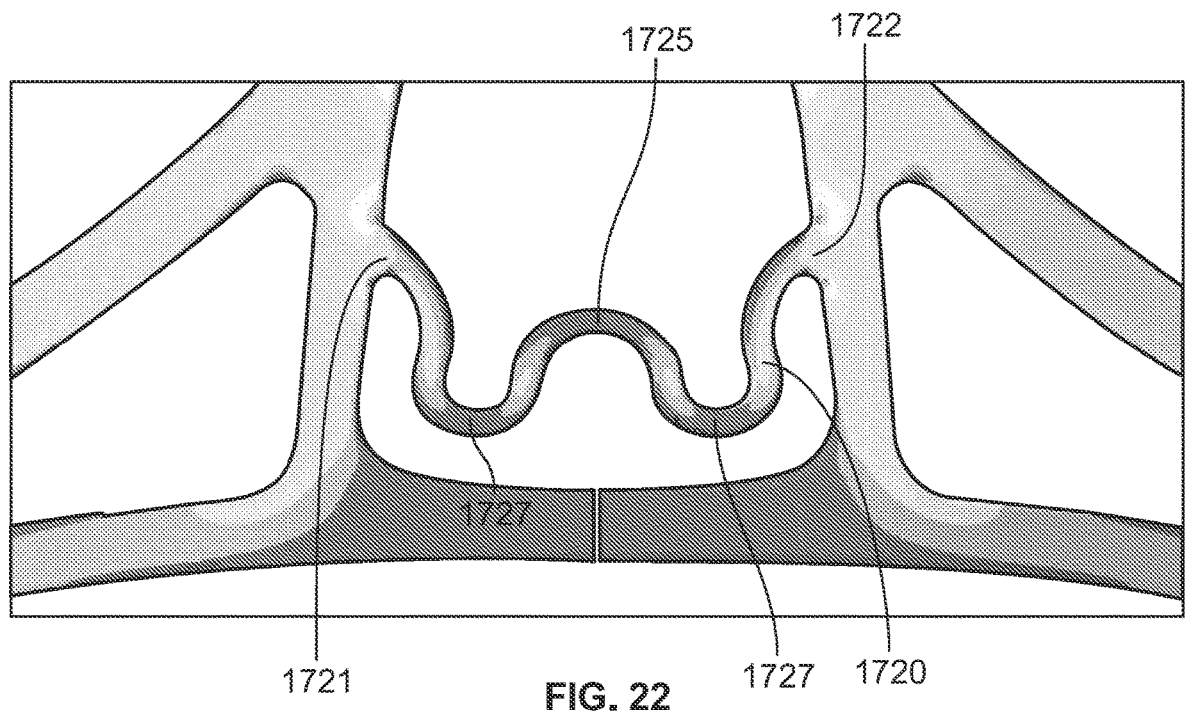

FIG. 22 shows a frame with an alternative embodiment of a stabilizing strut 1720. Stabilizing strut 1720 is connected to the frame at first end 1721 and at second end 1722. First and second ends 1721, 1722 each extend into a trough 1727 such that stabilizing strut 1720 includes two troughs 1727 and one peak 1725 positioned between and connecting troughs 1727. Troughs 1727 and peak 1725 each have a generally rounded shape. Peak 1725 has a width in the circumferential direction that is greater than the width of troughs 1727.

Figure 23A:
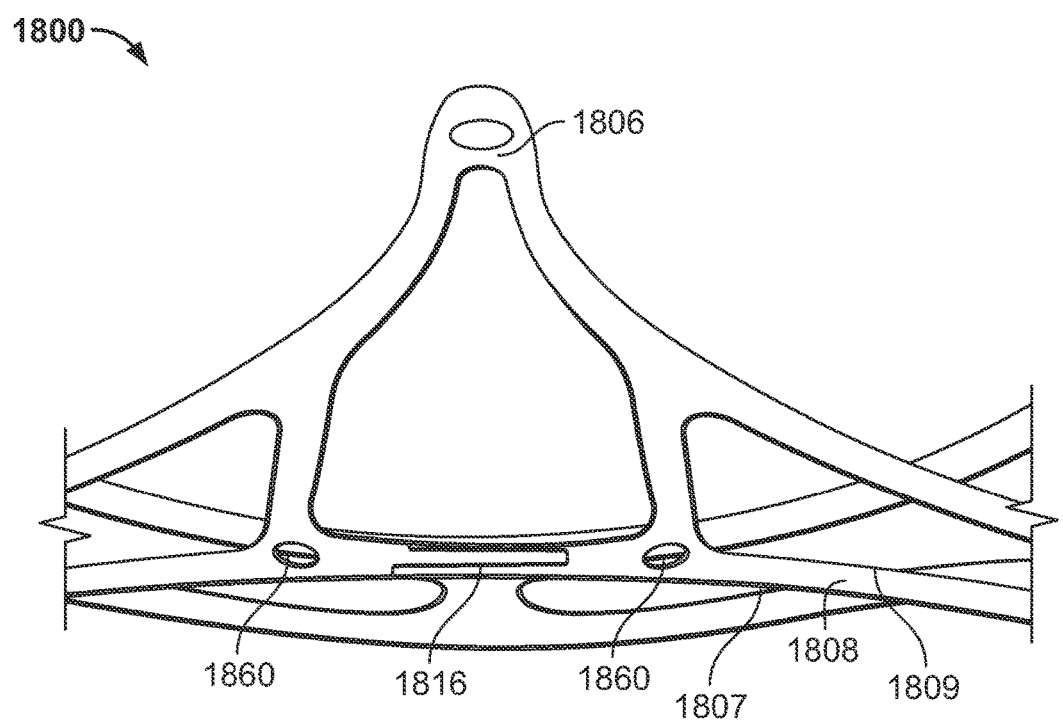
FIGS. 23A and 23B are a partial perspective side view and an enlarged view, respectively, of a weakened portion of a frame in accordance with an embodiment of the present disclosure.
Figure 23B:
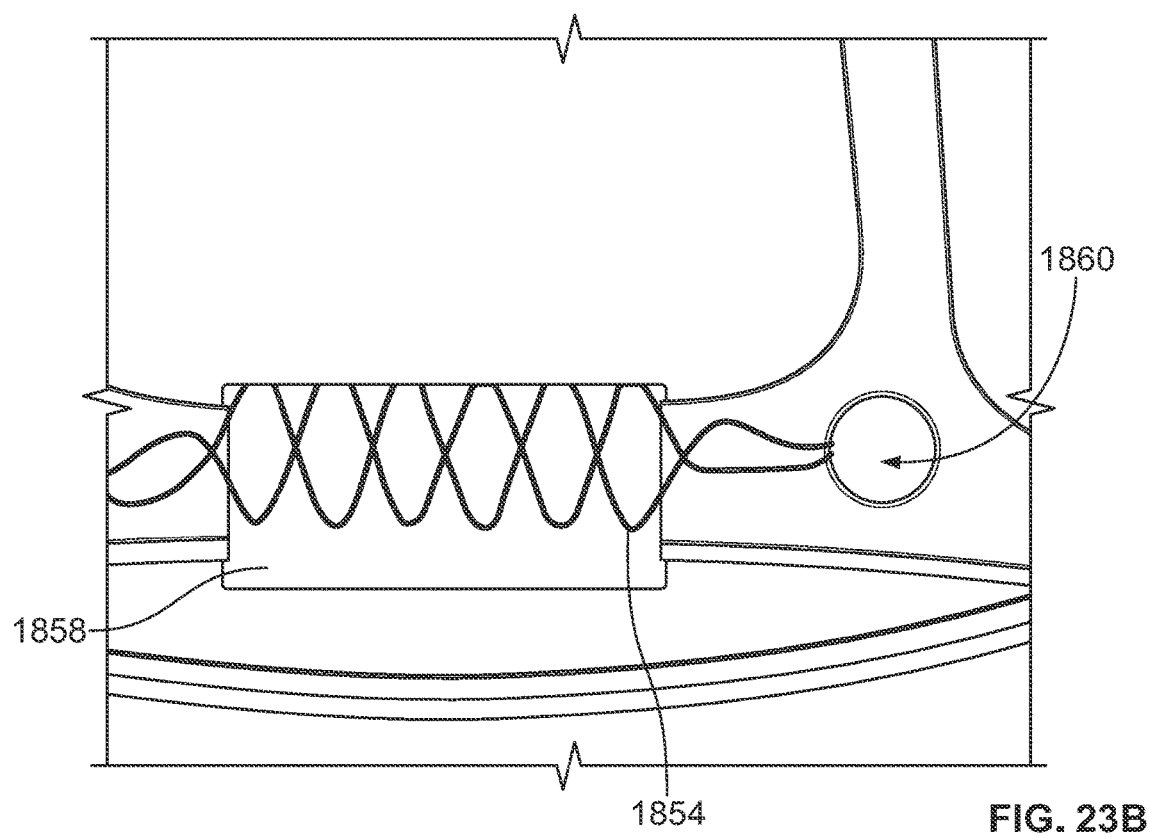

FIG. 23A shows an expandable frame 1800 according to another embodiment of the present disclosure. Frame 1800 includes a "Z" shaped slit 1816 formed in inflow portion 1808. Slit 1816 includes a first portion that extends in the height direction of inflow portion 1808 from top edge 1809 to a point about halfway to inflow edge 1807, a second portion that extends in the height direction of the inflow portion from the inflow edge to a point about halfway to the top edge, and a third portion that extends in the circumferential direction of frame 1800 and connects the first and second portions of the slit. An aperture 1860 is positioned on each end of slit 1816 so that a flexible member, such as suture or wire, may be secured through the apertures to hold frame 1800 together while allowing the frame to expand in a subsequent VIV surgery. As with the other frames described above, frame 1800 may include a single slit 1816 or a plurality of such slits. Moreover, slits 1816 may be positioned anywhere along the circumference of frame 1800, including below a commissure post 1806, as shown in FIG. 23A, or midway between adjacent commissure posts. FIG. 23B shows frame 1800 with sleeve 1858 positioned around slit 1816. Suture 1854 is connected to frame 1800 and/or sleeve 1858 and through apertures 1860 to hold the frame in a general annular shape while allowing expansion of the frame 1800.

Figure 24:
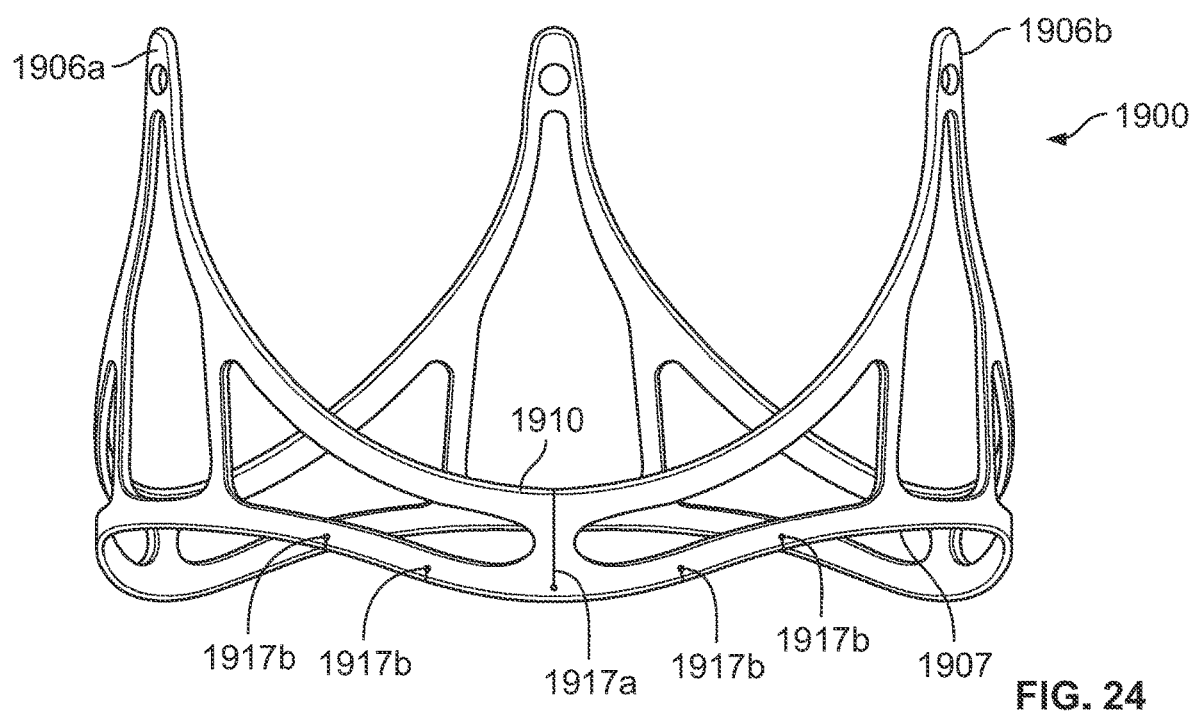
FIG. 24 is a side view of a frame of a prosthetic heart valve having weakened portions according to another embodiment of the present disclosure.

FIG. 24 shows an expandable frame 1900 having a plurality of slits 1917 positioned circumferentially between commissure posts 1906a and 1906b. One slit 1917a of the plurality of slits 1917 extends only through outflow edge 1910 while the other slits 1917b extend only through inflow edge 1907. Slit 1917a is positioned at about the midpoint between commissure posts 1906a and 1906b. This arrangement of slits spreads the stresses along the circumference of frame 1900 as weak points to break are created.

In a variant of the present disclosure, any of the frames described above may include a ring positioned around the outside of the frame to form the heart valve. Examples of such rings are shown in FIGS. 25-28. Each ring is positioned around an outer surface of the frame near the inflow portion of the frame. Each ring is scalloped with a shape that rises and falls to match the scalloped shape of the inflow portion of the frame. The ring is provided to help prevent the ovalization of the frame and may be radiopaque to enhance identification of the inflow portion of the heart valve under fluoroscopy to facilitate the proper positioning of the valve during initial implantation. The ring may be assembled to the frame by separately wrapping the frame and the ring in fabric and then stitching the two fabrics are stitched to the bottom of the frame.

Each of the rings of the present disclosure is expandable and may be positioned around any of the frames described above. The rings may incorporate the same or different expansion features as the frame the ring is disposed around. Thus, in some embodiments, one expansion feature of the present disclosure may be employed to expand the frame after implantation, while a different expansion feature of the present disclosure may be employed to expand the ring. In other embodiments, the same expansion feature may be included on both the frame and the ring. In some embodiments, the expansion features of the rings can be radially aligned with the expansion features of the frame, but in other embodiments, the expansion features of the rings may not be aligned with the expansion features of the frame.

Figure 25A:
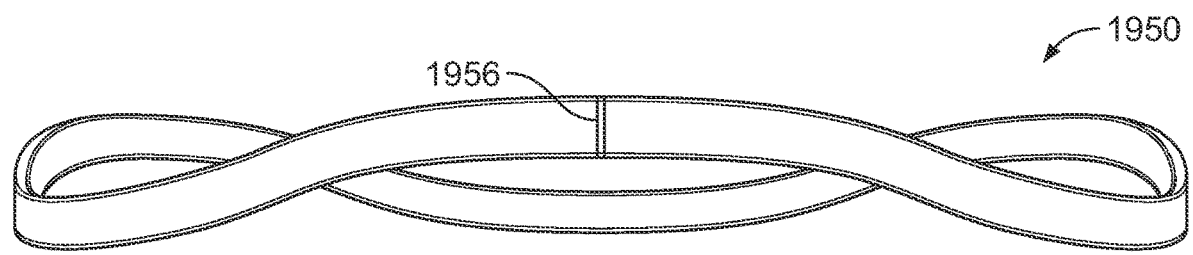
FIGS. 25A and 25B are side views of a ring to be used in conjunction with a frame to form a prosthetic heart valve according to another embodiment of the present disclosure.
Figure 25B:
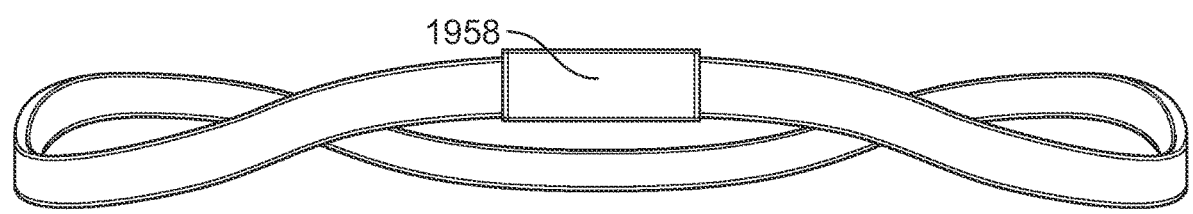

As shown in FIG. 25A, ring 1950 includes at least one through cut 1956, which extends through the height of the ring. Through cut 1956 is a simple cut through the thickness of ring 1950 such that the through cut defines two free, unconnected ends. A fabric covering (not shown) may be wrapped around the ring and surround the through cut 1956 to maintain the alignment of the ring and hold it together as one piece. As an alternative to fabric wrapped around the ring, a pre-formed sleeve 1958, shown in FIG. 25B, may be slid over one free end of the ring and then the other free end of the ring, so that both free ends are disposed within the sleeve. In such a configuration, sleeve 1958 maintains the annular shape of ring 1950. In a preferred arrangement, through cut 1956 may be positioned around the outer surface of the frame adjacent a weakened portion of the frame, e.g., adjacent any of the weakened portions described above.

Figure 26:
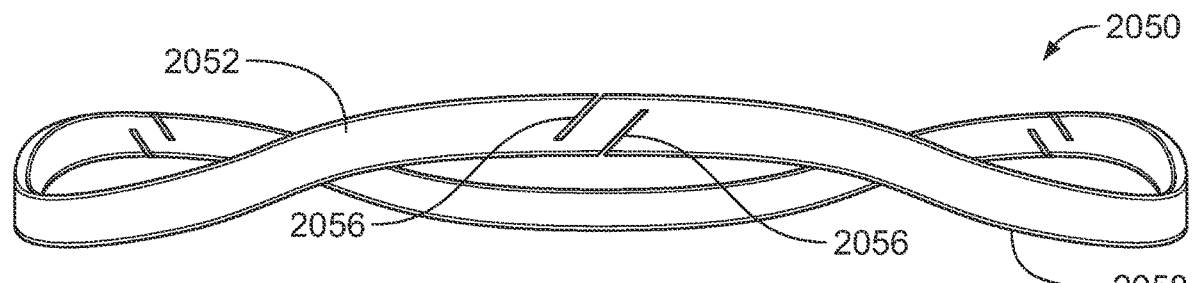
FIG. 26 is a side view of a ring according to another embodiment of the present disclosure.

FIG. 26 shows a ring 2050 that includes at least one pair of diagonal through cuts 2056 extending along a portion of the height of the ring, with one through cut extending downward from the top edge 2052 of the ring and the other through cut extending upward from the bottom edge 2058 of the ring. The through cuts 2056 in a pair of through cuts may extend parallel to one another.

Figure 27A:
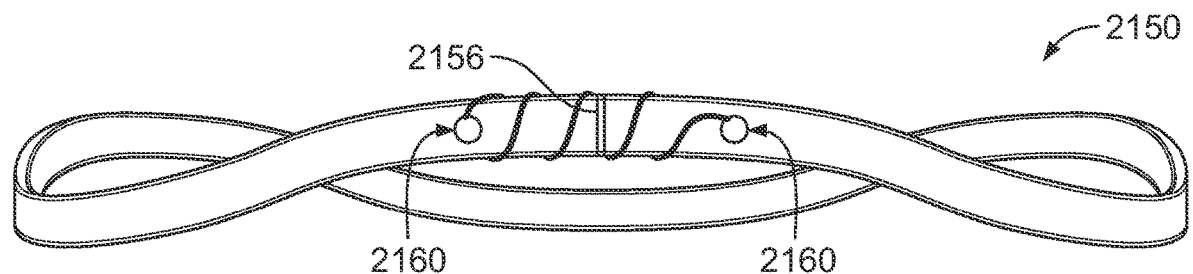
FIGS. 27A and 27B are side views of a ring according to another embodiment of the present disclosure.
Figure 27B:
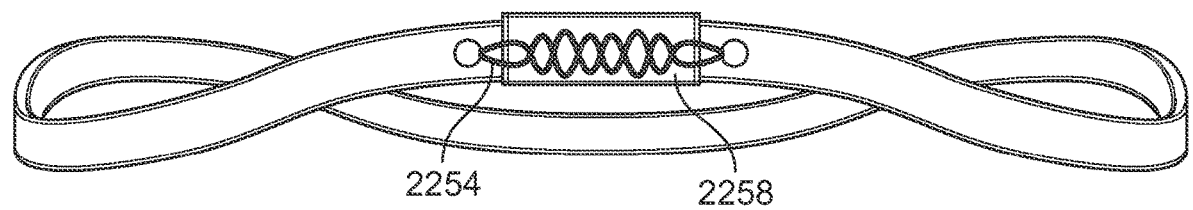

FIG. 27A shows a variant ring 2150 that includes a through cut 2156 extending through the thickness of the ring and through the height of the ring. An aperture 2160 is positioned on each side of through cut 2156, enabling a flexible member to be threaded through the apertures to hold ring 2150 together. The flexible member may be suture, wire or another preferably filamentary material connected to the ring tightly to maintain the radial strength of the ring. As shown in FIG. 27B, flexible member 2254 may be used in conjunction with a sleeve 2258 to hold the ends of ring 2250 in place. This configuration may provide additional support to ring 2250 as both sleeve 2258 and flexible member 2254 hold the ring together.

Figure 28:
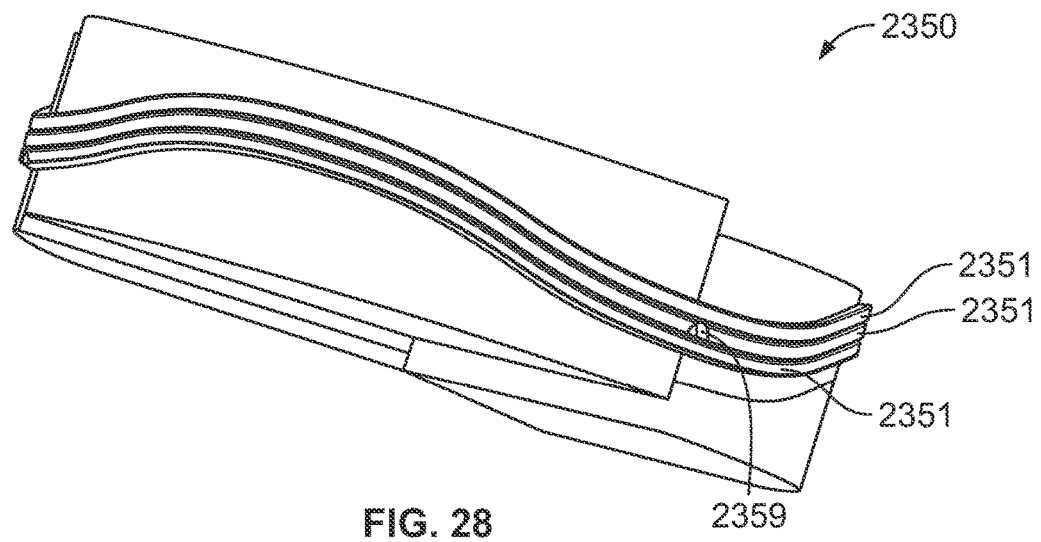
FIG. 28 is a perspective side view of a ring according to another embodiment of the present disclosure.

FIG. 28 shows another embodiment of a support ring for positioning around a valve. In this example, ring 2350 is formed of a plurality of independent rings 2351. In the illustrated embodiment, ring 2350 is formed of three independent, continuous rings 2351 secured together to form a single ring. Rings 2351 include notches 2359 to propagate the breaking of the rings during expansion of the frame. When ring 2350 is positioned around a frame, notches 2359 may be circumferentially offset from the weakened portions of the frame to increase the strength of the frame and ring system. Alternatively, notches 2359 may be aligned with the weakened portions to allow easier expansion of the system. Although described with reference to three independent rings, in other examples there may be more or less independent rings. Alternatively, the independent rings may be nested together rather than secured to one another.

The frames described above may each form part of a surgical heart valve, such as heart valve 200 described above, and may be used in conjunction with the expandable rings. Such frames remain highly durable and may maintain about 80% of the radial force of the frame. The surgical heart valve may be implanted in a patient whose native valve does not function properly. The weakened areas of the frame and the ring are designed to remain substantially intact and not deform during the implantation of the surgical heart valve. After a period of time, the surgical heart valve itself may cease to function as intended and may no longer meet the needs of the patient. In some cases, the patient may be older and no longer able to tolerate the trauma of open chest, open heart surgery to replace the surgical heart valve. In such event, a collapsible transcatheter heart valve may be implanted using a less traumatic percutaneous procedure. In such procedure, the transcatheter heart valve is advanced to the target site in a collapsed condition, typically using a transfemoral or transapical approach, and deployed within the failing surgical valve.

In one embodiment, the transcatheter valve may be balloon expandable, and a deployment device may be used to deliver the valve and a dilation balloon to the target site. The transcatheter valve may be deployed within the failing valve, and the balloon may be expanded within the transcatheter valve, exerting a radially outward force that expands the collapsed valve. As the balloon applies the radially outward force to the transcatheter valve, the expanding valve transmits that force to the failing surgical valve. The exertion of that force on frames 1200-1900 causes the slits or perforations therein to deform, e.g., widen or break, such that the diameter of the frame symmetrically expands from a relatively small initial diameter to a relatively large expanded diameter. The weakened portions, i.e., the slits or perforations, may be sized and dimensioned such that they fail at a relatively low stress. As a result, a lower pressure balloon may be used to apply the appropriate expansion force to the transcatheter valve and the frame of the surgical valve. Generally, the frames are designed to begin expanding at about 2 atmospheres of pressure and are fully expanded with about 8 atmospheres of pressure. This may help to prevent rupture of the tissue of the native annulus, which is more likely to occur if the frame is over-expanded. Once the transcatheter valve and the surgical valve frame have expanded, an evaluation can be made as to the adequacy of blood flow therethrough.

In another embodiment, the transcatheter valve may be self-expanding and may expand upon deployment within the failing surgical valve. The expansion of the transcatheter valve applies a force on the surgical valve, causing the slits or perforations therein to widen or break and the surgical valve to also expand. As a result, the transcatheter valve is able to expand to a sufficiently-sized diameter. In a variant of this embodiment, the surgical valve may be expanded by a dilating balloon before the self-expanding transcatheter valve is deployed and expands.

In a variant embodiment in which the transcatheter valve includes an expandable ring, the process is the same as that described above, and the ring along with the frame expands to a second diameter larger than an initial diameter.

To summarize the foregoing, according to a first aspect of the disclosure, a prosthetic heart valve includes a non-collapsible annular frame extending in a longitudinal direction between an inflow edge and an outflow edge, the frame having a plurality of annularly spaced commissure posts adjacent the outflow edge, a flow direction through the frame extending from the inflow edge toward the outflow edge, the frame having a weakened portion such that the frame is expandable from an initial condition having a first diameter to an expanded condition having a second diameter larger than the first diameter when a radial outward force is applied to an inner surface of the frame; and a valve assembly connected to the frame and including a plurality of leaflets; and/or the frame may include a stabilizing strut positioned between the weakened portion and an associated commissure post; and/or the stabilizing strut may have a substantially U-shape; and/or the stabilizing strut may have a first height in the longitudinal direction in the initial condition of the frame and a second height in the longitudinal direction in the expanded condition of the frame, the first height being greater than the second height; and/or the stabilizing strut may have a first width in a circumferential direction in the initial condition of the frame and a second width in the circumferential direction in the expanded condition of the frame, the first width being less than the second width; and/or the stabilizing strut may have an apex positioned adjacent the weakened portion of the frame; and/or the stabilizing strut may have an inverted substantially U-shape; and/or the stabilizing strut may have a wave shape; and/or in the expanded condition, the stabilizing strut may be plastically deformed; and/or the weakened portion may include a slit extending through a thickness of the frame; and/or the slit may have a first width in a circumferential direction when the frame is in the initial condition and a second width in the circumferential direction when the frame is in the expanded condition, the second width being greater than the first width; and/or the slit may be positioned between adjacent ones of the commissure posts in a circumferential direction of the frame; and/or the slit may be positioned at a midpoint between the adjacent ones of the commissure posts; and/or the slit may extend through the inflow edge and terminate at a position between the inflow edge and the outflow edge; and/or the frame may include an inflow portion positioned below one of the commissure posts, the inflow portion extending from the inflow edge to a top edge, and the slit may extend through the inflow edge and terminate at a position between the inflow edge and the top edge; and/or the slit may terminate at a rounded end having a perimeter enclosed within the inflow portion of the frame; and/or the slit may extend through the inflow edge and the outflow edge of the frame; and/or the frame may include an inflow portion positioned below one of the commissure posts, the inflow portion extending from the inflow edge to a top edge, and the entirety of the slit may be within the inflow portion of the frame such that the inflow edge and the top edge are uninterrupted by the slit; and/or the slit may be spaced apart from the outflow edge and the inflow edge such that the inflow and outflow edges are uninterrupted by the slit, and/or the weakened portion may include a plurality of perforations, each perforation extending through the thickness of the frame; and/or the plurality of perforations may be spaced apart from each other in a linear array between the inflow edge and the outflow edge of the frame; and/or each of the plurality of perforations may have a diameter, and the diameters may increase sequentially in the longitudinal direction; and/or adjacent ones of the perforations may be spaced apart by a distance, and each of the distances may be less than 0.005 inches; and/or the frame may include a pair of apertures extending through the frame, one of the apertures being positioned on one side of the weakened portion and another of the apertures being positioned on an opposite side of the weakened portion in a circumferential direction of the frame; and/or the prosthetic heart valve may further include an expandable ring positioned around an outer surface of the frame; and/or the ring may include a weakened region that enables the ring to expand; and/or the weakened region may include a slit extending through a thickness of the ring; and/or the weakened region may include a through cut extending from a top edge of the ring to a bottom edge of the ring, and the ring may include at least one aperture on each side of the through cut; and/or the prosthetic heart valve may further include a filament extending through the apertures of the ring and secured to the ring to maintain an annular shape of the ring.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic heart valve, comprising:
a non-collapsible annular frame extending in a longitudinal direction between an inflow edge and an outflow edge, the frame having a plurality of annularly spaced commissure posts adjacent the outflow edge, a flow direction through the frame extending from the inflow edge toward the outflow edge, the frame having a weakened portion such that the frame is expandable from an initial condition having a first diameter to an expanded condition having a second diameter larger than the first diameter when a radial outward force is applied to an inner surface of the frame; and a valve assembly connected to the frame and including a plurality of leaflets,
wherein the frame comprises a first strut and a second strut connecting one of the plurality of annularly spaced commissure posts to the inflow edge,
wherein the frame includes a stabilizing strut extending between and connecting the first strut and the second strut and independent of the weakened portion.

2. The prosthetic heart valve of claim 1, wherein the weakened portion includes a slit extending through a thickness of the frame.

3. The prosthetic heart valve of claim 2, wherein the slit has a first width in a circumferential direction when the frame is in the initial condition and a second width in the circumferential direction when the frame is in the expanded condition, the second width being greater than the first width.

4. The prosthetic heart valve of claim 2, wherein the slit is positioned between adjacent ones of the commissure posts in a circumferential direction of the frame.

5. The prosthetic heart valve of claim 4, wherein the slit is positioned at a midpoint between the adjacent ones of the commissure posts.

6. The prosthetic heart valve of claim 2, wherein the frame includes an inflow portion positioned below one of the commissure posts, the inflow portion extending from the inflow edge to a top edge, and the slit extends through the inflow edge and terminates at a position between the inflow edge and the top edge.

7. The prosthetic heart valve of claim 6, wherein the slit terminates at a rounded end having a perimeter enclosed within the inflow portion of the frame.

8. The prosthetic heart valve of claim 1, wherein the stabilizing strut has a substantially U-shape.

9. The prosthetic heart valve of claim 8, wherein the stabilizing strut has a first height in the longitudinal direction in the initial condition of the frame and a second height in the longitudinal direction in the expanded condition of the frame, the first height being greater than the second height.

10. The prosthetic heart valve of claim 8, wherein the stabilizing strut has a first width in a circumferential direction in the initial condition of the frame and a second width in the circumferential direction in the expanded condition of the frame, the first width being less than the second width.

11. The prosthetic heart valve of claim 2, wherein the slit extends through the inflow edge and the outflow edge of the frame.

12. The prosthetic heart valve of claim 2, wherein the frame includes an inflow portion positioned below one of the commissure posts, the inflow portion extending from the inflow edge to a top edge, the entirety of the slit being within the inflow portion of the frame such that the inflow edge and the top edge are uninterrupted by the slit.

13. The prosthetic heart valve of claim 12, wherein the slit is spaced apart from the outflow edge and the inflow edge such that the inflow and outflow edges are uninterrupted by the slit.

14. The prosthetic heart valve of claim 1, wherein the weakened portion includes a plurality of perforations, each perforation extending through the thickness of the frame.

15. The prosthetic heart valve of claim 14, wherein the plurality of perforations are spaced apart from each other in a linear array between the inflow edge and the outflow edge of the frame.

16. The prosthetic heart valve of claim 15, wherein each of the plurality of perforations has a diameter, the diameters increasing sequentially in the longitudinal direction.

17. The prosthetic heart valve of claim 1, further comprising an expandable ring configured to be positioned around an outer surface of the frame.

18. The prosthetic heart valve of claim 17, wherein the ring includes a weakened region that enables the ring to expand.

19. The prosthetic heart valve, comprising:
a non-collapsible annular frame extending in a longitudinal direction between an inflow edge and an outflow edge, the frame having a plurality of annularly spaced commissure posts adjacent the outflow edge, a flow direction through the frame extending from the inflow edge toward the outflow edge, the frame having a weakened portion such that the frame is expandable from an initial condition having a first diameter to an expanded condition having a second diameter larger than the first diameter when a radial outward force is applied to an inner surface of the frame; and a valve assembly connected to the frame and including a plurality of leaflets,
wherein the frame includes a stabilizing strut positioned between the weakened portion and an associated commissure post,
wherein the stabilizing strut has a substantially U-shape, and
wherein the stabilizing strut has an apex positioned adjacent the weakened portion of the frame.

* * * * *